US012642513B2

(12) United States Patent

Holcombe et al.

(10) Patent No.: US 12,642,513 B2

(45) Date of Patent: Jun. 2, 2026

(54) KIT, METHOD, AND DEVICE FOR SAMPLING ORAL MICROBIOME

(71) Applicant: MARS, INCORPORATED, McLean, VA (US)

(72) Inventors: Lucy Jane Holcombe, Melton Mowbray (GB); Corryn Victoria Wallis, Melton Mowbray (GB); Avika Kishorlal Ruparell, Melton Mowbray (GB); Frank Edward Mars, McLean, VA (US)

(73) Assignee: MARS, INCORPORATED, McLean, VA (US)

( * ) Notice: Subject to any disclaimer, the term of this patent is extended or adjusted under 35 U.S.C. 154(b) by 767 days.

(21) Appl. No.: 17/426,292

(22) PCT Filed: Feb. 3, 2020

(86) PCT No.: PCT/US2020/016445

§ 371 (c)(1),
(2) Date: Jul. 28, 2021

(87) PCT Pub. No.: WO2020/160555

PCT Pub. Date: Aug. 6, 2020

(65) Prior Publication Data

US 2021/0401408 A1 Dec. 30, 2021

Related U.S. Application Data

(60) Provisional application No. 62/867,595, filed on Jun. 27, 2019, provisional application No. 62/800,328, filed on Feb. 1, 2019.

(51) Int. Cl.
| | |
|---|---|
| *A61B 10/00* | (2006.01) |
| *C12Q 1/689* | (2018.01) |

(Continued)

(52) U.S. Cl.
CPC ...... *A61B 10/0051* (2013.01); *A61B 10/0096* (2013.01); *C12Q 1/689* (2013.01);
(Continued)

(58) Field of Classification Search
CPC ............ A61B 10/0051; A61B 10/0096; A61B 2010/0216
See application file for complete search history.

(56) References Cited

U.S. PATENT DOCUMENTS

| | | | | |
|---|---|---|---|---|
| 2007/0249961 A1* | 10/2007 | Morrison | ............... | A61B 50/22 |
| | | | | 600/572 |
| 2008/0058677 A1 | 3/2008 | Yong | | |

(Continued)

FOREIGN PATENT DOCUMENTS

| | | |
|---|---|---|
| EP | 1 405 599 A1 | 4/2004 |
| GB | 1 045 845 A | 10/1966 |

(Continued)

OTHER PUBLICATIONS

Butkovic et al., "Dental Diseases of Dogs: a Retrospective Study of Radiological Data," Acta Veterinaria Brno, 70:203-208 (2001).

(Continued)

*Primary Examiner* — Tse W Chen
*Assistant Examiner* — Martin Nathan Ortega
(74) *Attorney, Agent, or Firm* — Baker Botts L.L.P.

(57) ABSTRACT

Disclosed herein are kits and related methods for testing the oral microbiome of an animal for presence of one or more bacteria, e.g, associated with an oral disease or disorder, such periodontal disease, good oral health, or both, in a sample collected from the animal. The kit includes a sample collection device having a handle and a head opposite the handle. The kit further includes a dry container for storing (Continued)

the sample collection device. The container has an open position for receiving at least a portion of the head and a closed position.

19 Claims, 16 Drawing Sheets

(51) Int. Cl.

| | |
|---|---|
| *G01N 1/02* | (2006.01) |
| *A61B 10/02* | (2006.01) |
| *G01N 1/10* | (2006.01) |

(52) U.S. Cl.
CPC ........ *G01N 1/02* (2013.01); *A61B 2010/0216* (2013.01); *A61B 2503/40* (2013.01); *G01N 2001/028* (2013.01); *G01N 2001/1031* (2013.01); *G01N 2800/18* (2013.01)

(56) References Cited

U.S. PATENT DOCUMENTS

| | | | |
|---|---|---|---|
| 2008/0183395 A1* | 7/2008 | Bevilacqua .......... | C12Q 1/6883 |
| | | | 435/6.16 |
| 2011/0004122 A1 | 1/2011 | Sangha | |
| 2013/0116596 A1 | 5/2013 | Birnboim et al. | |
| 2013/0302219 A1* | 11/2013 | Li ....................... | B01L 3/50825 |
| | | | 422/550 |
| 2013/0338533 A1* | 12/2013 | Olsen ................ | A61B 10/0291 |
| | | | 600/569 |
| 2016/0243544 A1* | 8/2016 | Hu ........................ | B01L 3/5029 |
| 2017/0175172 A1 | 6/2017 | Apte et al. | |
| 2017/0235902 A1* | 8/2017 | Almonacid ............ | G16B 40/20 |
| | | | 435/6.15 |
| 2018/0003598 A1* | 1/2018 | Xie ........................ | A61B 10/02 |
| 2018/0030516 A1* | 2/2018 | Nawana ............... | C12Q 1/6806 |
| 2018/0103935 A1* | 4/2018 | Pringle ................ | H01J 49/025 |
| 2020/0113550 A1* | 4/2020 | Sessions ............ | A61B 10/0283 |
| 2020/0149115 A1* | 5/2020 | Dobak .................... | A61P 35/00 |

FOREIGN PATENT DOCUMENTS

| | | |
|---|---|---|
| GB | 2 383 955 A | 7/2003 |
| IT | MI20 100 796 A1 | 11/2011 |
| WO | WO 2007/009414 A1 | 1/2007 |
| WO | WO 2008/137506 A2 | 11/2008 |
| WO | WO 2014/199115 A1 | 12/2014 |

OTHER PUBLICATIONS

Davis et al., "A Cross-Sectional Survey of Bacterial Species in Plaque from Client Owned Dogs with Healthy Gingiva, Gingivitis or Mild Periodontitis," PLoS One, 8(12):e83158 (2013).

Dewhirst et al., "The Canine Oral Microbiome," PLoS One, 7(4):e36067 (2012).

Dewhirst et al., "The feline oral microbiome: a provisional 16S rRNA gene based taxonomy with full-length reference sequences," Vet Microbiol, 175:294-303 (2015).

Hamp et al., "A macroscopic and radiologic investigation of dental diseases of the dog," Veterinary Radiology, 25(2):86-92 (1984).

Harris et al., "A Pyrosequencing Investigation of Differences in the Feline Subgingival Microbiota in Health, Gingivitis and Mild Periodontitis," PLoS One, 10(11):e0136986 (2015).

Hoffman et al., "Epidemiology of periodontal disease in poodles," Journal of Small Animal Practice, 37:309-316 (1996).

International Search Report mailed Jul. 6, 2020 in International Application No. PCT/US2020/016445.

Kortegaard et al., "Periodontal disease in research beagle dogs—an epidemiological study," J Small Anim Pract, 49:610-616 (2008).

Lund et al., "Health status and population characteristics of dogs and cats examined at private veterinary practices in the United States," J Am Vet Med Assoc, 214:1336-1341 (1999).

O'Neill et al., "Prevalence of Disorders Recorded in Dogs Attending Primary-Care Veterinary Practices in England," PLoS One, 9(3):e90501 (2014).

Ott et al., "Quantification of Intestinal Bacterial Populations by Real-Time PCR with a Universal Primer Set and Minor Groove Binder Probes: a Global Approach to the Enteric Flora," J. Clin. Microbiol. 42(6):2566-2572 (2004).

Riggio et al., "Molecular identification of bacteria associated with canine periodontal disease," Vet Microbiol, 150(3-4):394-400 (2011).

Wallis et al., "A longitudinal assessment of changes in bacterial community composition associated with the development of periodontal disease in dogs," Vet Microbiol, 181:271-282 (2015).

\* cited by examiner

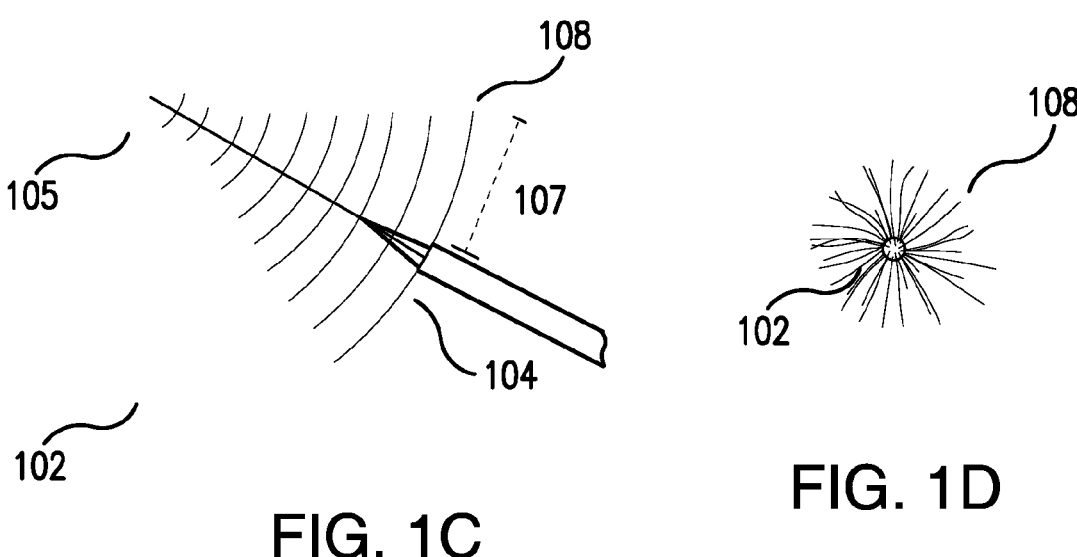
FIG. 1C
FIG. 1D
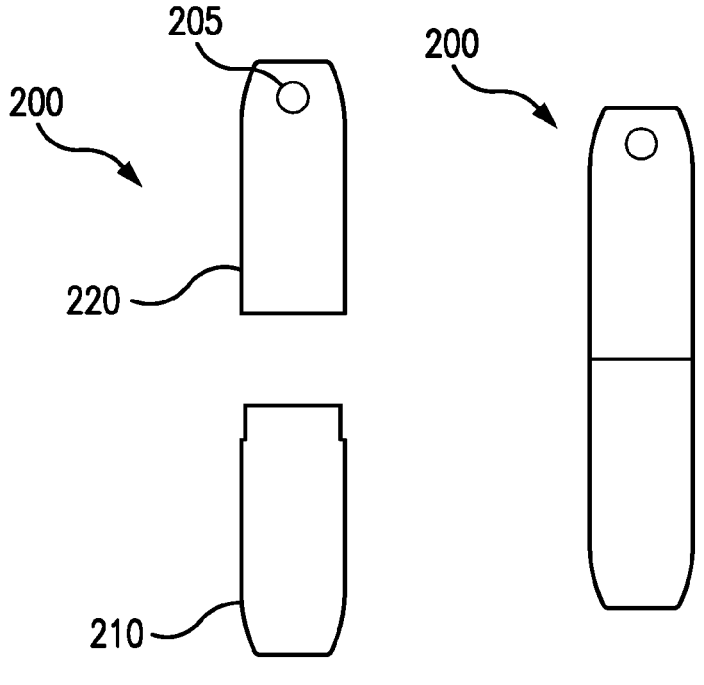
FIG. 2A
FIG. 2B

FIG. 2C          FIG. 2D

KIT, METHOD, AND DEVICE FOR SAMPLING ORAL MICROBIOME

CROSS-REFERENCE TO RELATED APPLICATIONS

This application is a U.S. National Stage Patent Application under 35 U.S.C. § 371 of International Patent Application No. PCT/US2020/016445, filed on Feb. 3, 2020, which claims the benefit of priority to U.S. Patent Application No. 62/800,328, filed on Feb. 1, 2019, and U.S. Patent Application No. 62/867,595, filed on Jun. 27, 2019, the contents of each of which are hereby incorporated herein by reference in their entireties, and to each of which priority is claimed.

FIELD

The presently disclosed subject matter relates to a kit, method, and tool for sampling bacteria from an animal's oral cavity. The presently disclosed subject matter further relates to a sample collection device for sampling bacteria from an animal's oral cavity, as well as related diagnostic methods.

BACKGROUND

Gum disease, such as periodontal disease, is commonly seen in veterinary treatment, with prevalence of such disease estimated between 9% and 20% [1, 2]. Higher prevalence, between 44% and 100%, has been reported in studies of anesthetized dogs and through examination of post-mortem samples [3-6]. These data imply that the disease is under-diagnosed in veterinary treatment, where the majority of examinations are performed on conscious dogs.

Bacterial species in dental plaque that are associated with periodontal health and disease are known in the art [7-12]. For example, International Publication No. WO 2008/137506, incorporated herein by reference in its entirety, describes presence or absence of at least one microorganism, from a sample from the mouth of a dog, wherein the microorganism which is associated with periodontal disease in a dog is one or more disease-associated microorganisms selected from: *Peptostreptococcus* sp., *Synergistes* sp., *Clostridiales* sp., *Eubacterium nodatum, Selenomonas* sp., *Bacteroidetes* sp., *Odoribacter denticanis, Desulfomicrobium ovale, Moraxella* sp., *Bacteroides denticanoris, Fillifactor villosus, Porphyromonas canoris, Porphyromonas gulae, Treponema denticola*, and *Porphyromonas salivosa*. International Publication No. WO 2014/199115, incorporated herein by reference in its entirety, further describes bacteria associated with disease, particularly periodontal disease, and with good oral health.

A number of techniques have been developed to assess oral disease and disorders, such as periodontal disease. Such techniques include, but are not limited to, probing of the gums and acquiring intra-oral dental radiographs. However, such methods and techniques require animals to be given a general anesthetic, require highly trained individuals, and are costly. Additionally, such methods can be stressful for both the subject animal and the owner of the subject animal. The development of a device, kit, and method for the diagnosis of an oral disease or disorder, such as periodontal disease, in conscious animals would therefore be appealing to both veterinarians and owners and would improve animal welfare.

Diagnostic testing kits usually require the collection of a DNA sample from the subject. However, these tests frequently require that the DNA sample is stored in a buffer to ensure DNA stability. For example, commercially available sample collection kits that require buffers include OMNIgene•ORAL (OMR-110) by DNA Genotek, Inc. (Ottawa, CA) and Stool Collection Tube with DNA Stabilizer by Invitek Molecular GmbH (Berlin, DE). Storing samples in a liquid such as a buffer can introduce safety and convenience concerns during the transportation of such samples. Storing a sample in buffer can also be difficult for the user during the sample collection process, as the user must take care to ensure that the buffer is not spilled during the collection of the sample; if the buffer is spilled, another kit would have to be purchased to collect the sample. Including a buffer can also increase costs and raise concerns for contamination, and the use of a buffer requires a sealed or hermetically sealed container.

Accordingly, there exists a need for an improved device, kit and method for the diagnosis of an oral disease or disorder (e.g., periodontal disease) in animals.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages, and in accordance with the purpose of the disclosed subject matter, as embodied and broadly described, the disclosed subject matter includes in one aspect a kit to test the oral microbiome of an animal. The kit includes: a sample collection device having a handle and a head opposite the handle; and a dry container for storing the sample collection device, the container having an open position for receiving at least a portion of the head and a closed position, wherein the dry container defines an aperture to permit communication between an inside of the dry container with an external environment. In some embodiments, a longitudinal axis of the head is disposed at an angle with respect to a longitudinal axis of the handle between approximately 90 degrees and 170 degrees thereto. In some embodiments, the head has a cylindrical shape. In some embodiments, the head has a length dimension measured along a longitudinal axis, wherein the length dimension is between approximately 1.5 cm and 2.5 cm. In some embodiments, the head includes at least one of a swab, cotton, foam, nylon, polyester, rayon, and combinations thereof.

In further embodiments, the head includes bristles. In some embodiments, the bristles are configured to capture sample therebetween. In some embodiments, bristles extend over substantially 360 degrees of an outer surface of the head. In some embodiments, a length dimension of the bristles is between approximately 1.5 mm and 5 mm. In some embodiments, the bristles are of substantially similar length dimension. In some embodiments, bristles at a first end of the head proximate the handle are longer than bristles at a second end of the head distal to the handle. In some embodiments, length dimension tapers from the first end of the head to the second end of the head, the bristles defining a substantially conical shape.

In further embodiments, the sample collection device includes a cytology brush.

In another aspect, the present disclosure features a use of any of the kits disclosed herein, wherein the use includes swabbing the mouth of the animal with the sample collection device to collect a sample and drying the head and storing the sample collection device for a time t1. In some embodiments, the use further includes performing an assay on the sample to measure an amount of a microbial nucleic acid to detect one or more bacteria and/or to measure an amount of one or more bacteria in the sample. In some embodiments, the head is air dried after the sample is collected. In certain embodiments, the head is air dried at room temperature. In further embodiments, swabbing the mouth of the animal includes brushing or swabbing at least one of the gums, the gum-line, the teeth, the tongue, the roof of the mouth, and/or another part of the oral cavity. In some embodiments, a is up to about 14 days after the sample is collected. In some embodiments, the sample collection device is stored at a temperature of up to about 40° C. In some embodiments, the one or more bacteria is found in an oral microbiome of the animal. In some embodiments, the one or more bacteria includes bacteria associated with an oral disease or disorder, bacteria associated with good oral health, or both. For example, in some embodiments, the one or more bacteria includes Peptostreptococcaceae sp., volatile organic compound producing bacteria, or both. In particular embodiments, the one or more bacteria includes Peptostreptococcaceae XIII [G-1] sp., Peptostreptococcaceae COT-030, Peptostreptococcaceae COT-005/004, Peptostreptococcaceae COT-047, and/or Peptostreptococcaceae COT-019. In further embodiments, the use further includes diagnosing a likelihood of the animal having an oral disease or disorder if the one or more bacteria detected is indicative of poor or worsening oral health. In some embodiments, the use further includes recommending a change in oral hygiene or an intervention if the one or more bacteria detected is indicative of poor or worsening oral health. In some embodiments, the intervention includes cleaning the mouth of the animal (such as by tooth brushing), removing plaque from the mouth of the animal, polishing the teeth of the animal, scaling the teeth to remove tartar or calculus, performing a gingivectomy, removing one or more diseased teeth from the mouth of the animal, administering an antibiotic, an anti-inflammatory drug, and/or an analgesic to treat an oral infection, providing dental chews to the animal or increasing frequency of dental chews, introducing or increasing frequency of non-edible chewing toys and dispensers, introducing or increasing frequency of tooth brushing, increasing use of dental diets, providing a dental treatment solution in water, or any combination thereof. In certain embodiments, the sample is a plaque sample. In some embodiments, the animal is a companion animal. For example, in some embodiments, the animal is a dog or a cat. In some embodiments, the oral disease or disorder is periodontal disease, gingival stomatitis, odontoclastic resorptive lesions, and/or oral malodor.

In another aspect, the present disclosure features a kit as disclosed herein for use in assessing an oral health status of an animal, wherein the kit is used for swabbing the mouth of the animal with the sample collection device to collect a sample and drying the head and storing the sample collection device for a time t1. In some embodiments, the use of the kit further comprises performing an assay on the sample to measure an amount of a microbial nucleic acid to detect one or more bacteria and/or to measure an amount of one or more bacteria in the sample. In some embodiments, the head is air dried after the sample is collected. In some embodiments, the head is air dried at room temperature. In some embodiments, swabbing the mouth of the animal includes brushing or swabbing at least one of the gums, the gum-line, the teeth, the tongue, the roof of the mouth, and/or another part of the oral cavity. In some embodiments, t1 is up to about 14 days after the sample is collected. In further embodiments, the sample collection device is stored at a temperature of up to about 40° C. In some embodiments, the one or more bacteria is found in the oral microbiome of the animal. In some embodiments, the one or more bacteria comprises bacteria associated with an oral disease or disorder, bacteria associated with good oral health, or both. In some embodiments, the one or more bacteria includes Peptostreptococcaceae sp., volatile organic compound producing bacteria, or both. In particular embodiments, the one or more bacteria includes Peptostreptococcaceae XIII [G-1] sp., Peptostreptococcaceae COT-030, Peptostreptococcaceae COT-005/004, Peptostreptococcaceae COT-047, and/or Peptostreptococcaceae COT-019. In some embodiments, the kit for use further comprises diagnosing a likelihood of the animal having an oral disease or disorder if the one or more bacteria detected is indicative of poor or worsening oral health. In some embodiments, the kit for use further comprises recommending a change in oral hygiene or an intervention if the one or more bacteria detected is indicative of poor or worsening oral health. In some embodiments, the intervention comprises cleaning the mouth of the animal, removing plaque from the mouth of the animal, polishing the teeth of the animal, scaling the teeth to remove tartar or calculus, performing a gingivectomy, removing one or more diseased teeth from the mouth of the animal, administering an antibiotic, an anti-inflammatory drug, and/or an analgesic to treat an oral infection, providing dental chews to the animal or increasing frequency of dental chews, introducing or increasing frequency of non-edible chewing toys and dispensers, introducing or increasing frequency of tooth brushing, increasing use of dental diets, providing a dental treatment solution in water, or any combination thereof. In some embodiments, the sample is a plaque sample. In particular embodiments, the animal is a companion animal. In certain embodiments, the animal is a dog or a cat. In some embodiments, the oral disease or disorder is periodontal disease, gingival stomatitis, odontoclastic resorptive lesions, and/or oral malodor.

The disclosed subject matter also includes a method to use a kit to test the oral microbiome of an animal. The method includes providing a kit having a sample collection device with a handle and a head opposite the handle. The kit also includes a dry container for storing the sample collection device, the container having an open position for receiving at least a portion of the head and a closed position. The method further includes swabbing the mouth of an animal with the sample collection device to collect a sample, drying the head of the sample collection device, and storing the sample collection device.

In accordance with the disclosed subject matter, drying the head can include air drying the head after the sample is collected. For purpose of example and not limitation, the head can be air dried at room temperature. Additionally, or alternatively, swabbing the mouth of the animal can include brushing or swabbing at least one of the gums, the gum-line, the teeth, the tongue, the roof of the mouth, and/or other part of the oral cavity. For purpose of example, microorganisms and tissue of the animal swabbed can be collected by the sample collection device when the mouth of the animal is swabbed. The microorganisms collected can include, for example, bacteria, fungi, and viruses, and the tissue of the animal collected can include, for example oral epithelium cells.

Further in accordance with the disclosed subject matter, the method can include testing the sample for a presence of bacteria. Additionally, or alternatively, testing the sample for the presence of bacteria can include testing the sample for the presence or absence and amount of at least one of bacteria associated with an oral disease or disorder, bacteria associated with good oral health, or both. The method can further include testing the sample for the presence of at least one of bacteria (such as Peptostreptococcaceae sp., volatile organic compound producing bacteria, or both), fungi, viruses, or other microorganisms. In particular embodiments, the at least one bacteria is Peptostreptococcaceae XIII [G-1] sp. In some embodiments, the oral disease or disorder is periodontal disease, gingival stomatitis, odontoclastic resorptive lesions, and/or oral malodor.

The disclosed subject matter also includes a method to monitor the oral health of an animal. The method includes providing a first kit and a second kit, each of the first and second kit including a sample collection device and a dry container having the features described herein. The method further includes swabbing the mouth of an animal with a sample collection device to collect a first sample at a first time and swabbing the mouth of the animal with a sample collection device to collect a second sample at a second time. The method further includes testing the first sample and the second sample for the presence or absence and amount of at least one of bacteria associated with an oral disease or disorder (e.g., periodontal disease), bacteria associated with good oral health, or both. The method also includes comparing a first amount of bacteria associated with the oral disease or disorder, bacteria associated with good oral health, or both in the first sample with a second amount of bacteria associated with the oral disease or disorder, bacteria associated with good oral health, or both in the second sample to determine a difference between the first amount and the second amount. In some embodiments, the oral disease or disorder is periodontal disease, gingival stomatitis, odontoclastic resorptive lesions, and/or oral malodor.

In another aspect, the present disclosure features a method of collecting a sample from an oral cavity of an animal, the method including: (i) providing a kit including: (a) a sample collection device having a handle and a head opposite the handle; and (b) a dry container for storing the sample collection device, the container having an open position for receiving at least a portion of the head and a closed position, wherein the dry container defines an aperture to permit communication between an inside of the dry container with an external environment; (ii) swabbing a mouth of the animal with the sample collection device to collect the sample; and (iii) drying the head and storing the sample collection device for a time t1. In some embodiments, the method further includes (iv) performing an assay on the sample to measure an amount of a microbial nucleic acid to detect one or more bacteria and/or to measure an amount of one or more bacteria in the sample. In some embodiments, the one or more bacteria is found in an oral microbiome of the animal.

In another aspect, the present disclosure features a method of detecting one or more bacteria in an oral microbiome of an animal, the method including: (i) providing a kit including: (a) a sample collection device having a handle and a head opposite the handle; and (b) a dry container for storing the sample collection device, the container having an open position for receiving at least a portion of the head and a closed position, wherein the dry container defines an aperture to permit communication between an inside of the dry container with an external environment; (ii) swabbing the mouth of the animal with the sample collection device to collect a sample; (iii) drying the head and storing the sample collection device for a time t1; and (iv) performing an assay on the sample to measure an amount of a microbial nucleic acid to detect the one or more bacteria and/or to measure an amount of one or more bacteria in the sample.

In some embodiments of any of the preceding methods, the method further includes diagnosing a likelihood of the animal having an oral disease or disorder if the one or more bacteria detected is indicative of poor or worsening oral health. In some embodiments, the method further includes recommending a change in oral hygiene or an intervention if the one or more bacteria detected is indicative of poor or worsening oral health. In certain embodiments, the intervention includes cleaning the mouth of the animal (such as by tooth brushing), removing plaque from the mouth of the animal, polishing the teeth of the animal, scaling the teeth to remove tartar or calculus, performing a gingivectomy, removing one or more diseased teeth from the mouth of the animal, administering an antibiotic, an anti-inflammatory drug, and/or an analgesic to treat an oral infection, providing dental chews to the animal or increasing frequency of dental chews, introducing or increasing frequency of non-edible chewing toys and dispensers, introducing or increasing frequency of tooth brushing, increasing use of dental diets, providing a dental treatment solution in water, or any combination thereof.

In another aspect, the present disclosure features a method of monitoring an oral health of an animal, the method including: (i) providing a first kit and a second kit, each of the first and second kit including: (a) a sample collection device having a handle and a head opposite the handle; and (b) a dry container for storing the sample collection device, the container having an open position for receiving at least a portion of the head and a closed position, wherein the dry container defines an aperture to permit communication between an inside of the dry container with an external environment; (ii) swabbing the mouth of the animal with the sample collection device of the first kit to collect a first sample at a first time and swabbing the mouth of the animal with the sample collection device of the second kit to collect a second sample at a second time; (iii) drying the head and storing the sample collection device for a time t1; (iv) testing the first sample to detect a first amount of one or more bacteria and testing the second sample to detect a second amount of one or more bacteria, wherein the one or more bacteria includes bacteria associated with an oral disease or disorder, bacteria associated with good oral health, or both; and (v) comparing the first amount with the second amount to determine a difference between the first amount and the second amount. In some embodiments, the method further includes diagnosing a likelihood of the animal having an oral disease or disorder if the difference between the first sample and the second sample is indicative of poor or worsening oral health. In some embodiments, the method further includes recommending a change in oral hygiene or an intervention if the difference between the first sample and the second sample is indicative of poor or worsening oral health. In some embodiments, the intervention includes cleaning the mouth of the animal (such as by tooth brushing), removing plaque from the mouth of the animal, polishing the teeth of the animal, scaling the teeth to remove tartar or calculus, performing a gingivectomy, removing one or more diseased teeth from the mouth of the animal, administering an antibiotic, an anti-inflammatory drug, and/or an analgesic to treat an oral infection, providing dental chews to the animal or increasing frequency of dental chews, introducing or increasing frequency of non-edible chewing toys and dispensers, introducing or increasing frequency of tooth brushing, increasing use of dental diets, providing a dental treatment solution in water, or any combination thereof.

In another aspect, the present disclosure features a method of treating or preventing an oral disease or disorder in an animal in need thereof, the method including: (i) providing a kit including: (a) a sample collection device having a handle and a head opposite the handle; and (b) a dry container for storing the sample collection device, the container having an open position for receiving at least a portion of the head and a closed position, wherein the dry container defines an aperture to permit communication between an inside of the dry container with an external environment; (ii) diagnosing the animal with the oral disease or disorder and/or determining the likelihood of the animal developing the oral disease or disorder by: (a) swabbing the mouth of the animal with the sample collection device to collect a sample; (b) drying the head and storing the sample collection device for a time t1; and (c) performing an assay on the sample to measure an amount of a microbial nucleic acid to detect and/or to measure an amount of one or more bacteria indicative of the oral disease or disorder or indicative of poor or worsening oral health; and (iii) treating or preventing the oral disease or disorder in the animal by recommending a change in oral hygiene or an intervention. In some embodiments, intervention includes cleaning the mouth of the animal (such as by tooth brushing), removing plaque from the mouth of the animal, polishing the teeth of the animal, scaling the teeth to remove tartar or calculus, performing a gingivectomy, removing one or more diseased teeth from the mouth of the animal, administering an antibiotic, an anti-inflammatory drug, and/or an analgesic to treat an oral infection, providing dental chews to the animal or increasing frequency of dental chews, introducing or increasing frequency of non-edible chewing toys and dispensers, introducing or increasing frequency of tooth brushing, increasing use of dental diets, providing a dental treatment solution in water, or any combination thereof.

In yet another aspect, the present disclosure features a method of treating or preventing an oral disease or disorder in an animal in need thereof, the method including: (i) providing a first kit and a second kit, each of the first and second kit including: (a) a sample collection device having a handle and a head opposite the handle; and (b) a dry container for storing the sample collection device, the container having an open position for receiving at least a portion of the head and a closed position, wherein the dry container defines an aperture to permit communication between an inside of the dry container with an external environment; (ii) diagnosing the animal with the oral disease or disorder and/or determining the likelihood of the animal developing an the oral disease or disorder by: (a) swabbing the mouth of the animal with the sample collection device of the first kit to collect a first sample at a first time and swabbing the mouth of the animal with the sample collection device of the second kit to collect a second sample at a second time; (b) drying the head and storing the sample collection device for a time t1; (c) testing the first sample detect a first amount of one or more bacteria and testing the second sample to detect a second amount of one or more bacteria, wherein the one or more bacteria includes bacteria associated with an oral disease or disorder, bacteria associated with good oral health, or both; and (d) comparing the first amount with the second amount to determine a difference between the first amount and the second amount, wherein the difference between the first amount and the second amount is indicative of the oral disease or disorder, or is indicative of poor or worsening oral health; and (iii) treating or preventing the oral disease or disorder in the animal by recommending a change in oral hygiene or an intervention. In some embodiments, intervention includes cleaning the mouth of the animal (such as by tooth brushing), removing plaque from the mouth of the animal, polishing the teeth of the animal, scaling the teeth to remove tartar or calculus, performing a gingivectomy, removing one or more diseased teeth from the mouth of the animal, administering an antibiotic, an anti-inflammatory drug, and/or an analgesic to treat an oral infection, providing dental chews to the animal or increasing frequency of dental chews, introducing or increasing frequency of non-edible chewing toys and dispensers, introducing or increasing frequency of tooth brushing, increasing use of dental diets, providing a dental treatment solution in water, or any combination thereof.

In some embodiments of any of the methods disclosed herein, a longitudinal axis of the head is disposed at an angle with respect to a longitudinal axis of the handle between approximately 90 degrees and 170 degrees thereto. In some embodiments, the head has a cylindrical shape. In some embodiments, the head has a length dimension measured along a longitudinal axis, wherein the length dimension is between approximately 1.5 cm and 2.5 cm. In some embodiments, the head includes at least one of a swab, cotton, foam, nylon, polyester, rayon, and combinations thereof.

In further embodiments of any of the methods disclosed herein, the head includes bristles. In some embodiments, the bristles are configured to capture sample therebetween. In some embodiments, bristles extend over substantially 360 degrees of an outer surface of the head. In some embodiments, a length dimension of the bristles is between approximately 1.5 mm and 5 mm. In some embodiments, the bristles are of substantially similar length dimension. In some embodiments, bristles at a first end of the head proximate the handle are longer than bristles at a second end of the head distal to the handle. In particular embodiments, length dimension tapers from the first end of the head to the second end of the head, the bristles defining a substantially conical shape.

In some embodiments of any of the methods disclosed herein, the sample collection device includes a cytology brush. In some embodiments, the head is air dried after the sample is collected. For example, in some embodiments, the head is air dried at room temperature.

In further embodiments of any of the methods disclosed herein, swabbing the mouth of the animal includes brushing or swabbing at least one of the gums, the gum-line, the teeth, the tongue, the roof of the mouth, and/or another part of the oral cavity. In some embodiments, t1 is up to about 14 days after the sample is collected. In some embodiments, the sample collection device is stored at a temperature of up to about 40° C. In some embodiments, the one or more bacteria includes bacteria associated with an oral disease or disorder (e.g., periodontal disease), bacteria associated with good oral health, or both. In some embodiments, the one or more bacteria includes Peptostreptococcaceae sp., volatile organic compound bacteria, or both. In particular embodiments, the at least one bacteria is Peptostreptococcaceae XIII [G-1] sp., Peptostreptococcaceae COT-030, Peptostreptococcaceae COT-005/004, Peptostreptococcaceae COT-047, and/or Peptostreptococcaceae COT-019.

In some embodiments of any of the methods disclosed herein, the sample is a plaque sample. In some embodiments of any of the methods disclosed herein, the oral disease or disorder is periodontal disease, gingival stomatitis, odontoclastic resorptive lesions, and/or oral malodor.

In further embodiments of any of the methods disclosed herein, the animal is a companion animal. For example, in some embodiments, the animal is a dog or a cat.

In another aspect, the present disclosure features a kit to test the oral microbiome of an animal, the kit comprising: a sample collection device having a handle and a head opposite the handle; and a dry container for storing the sample collection device, the container having an open position for receiving at least a portion of the head and a closed position, wherein the dry container further includes a moisture absorbing device.

In yet another aspect, the present disclosure features a kit comprising: a sample collection device having a handle and a head opposite the handle; and a dry container for storing the sample collection device, the container having an open position for receiving at least a portion of the head and a closed position, wherein the dry container defines an aperture to permit communication between an inside of the dry container with an external environment; wherein the sample collection device is used to collect a sample from the gums, the gum-line, the teeth, the tongue, and/or the roof of the mouth of an animal, and wherein the sample comprises one or more bacteria associated with an oral disease or disorder, good oral health, or both. In some embodiments, the one or more bacteria comprises Peptostreptococcaceae COT-030.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the kits and methods of the disclosed subject matter. Together with the description, the drawings serve to explain the principles of the disclosed subject matter.

BRIEF DESCRIPTION OF THE FIGURES

FIG. 1C is a perspective partial detail view depicting the head of the sample collection device of FIG. 1A.

FIG. 1D is a front view of the sample collection device of FIG. 1A.

FIG. 2A is a front view of an exemplary embodiment of a dry container in an open position in accordance with the disclosed subject matter.

FIG. 2B is a front view of the dry container of FIG. 2A in a closed position.

FIG. 2C is a front view of a dry container in a closed position according to another embodiment.

FIG. 2D is a front view of a dry container in an open position with a sample collection device therein with according to another embodiment.

DETAILED DESCRIPTION

Figure 1A:
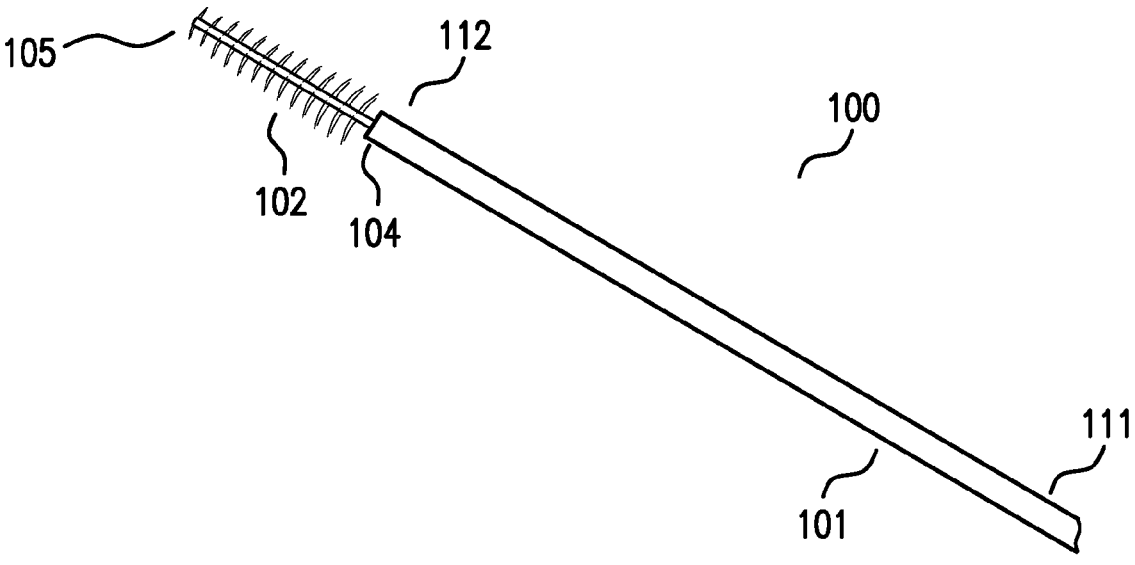
FIG. 1A is a perspective view of an exemplary embodiment of a sample collection device in accordance with the disclosed subject matter.
Figure 1B:
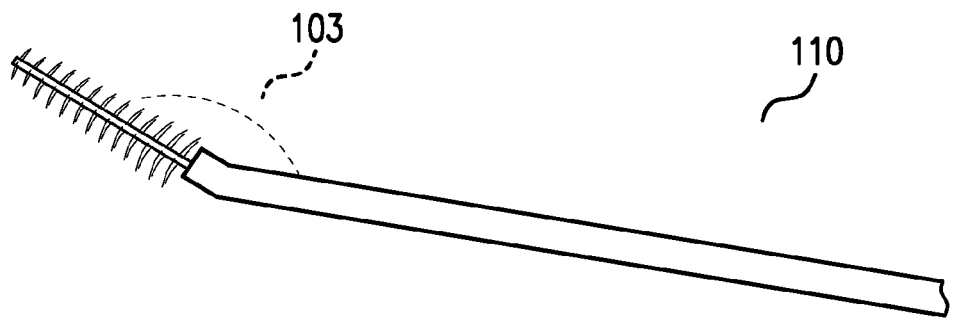
FIG. 1B is a perspective view of another exemplary embodiment of a sample collection device in accordance with the disclosed subject matter.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system.

The presently disclosed subject matter relates to kits, methods, and devices for sampling the oral microbiome and monitoring oral health in animals. The presently disclosed subject matter is particularly suited for sampling the oral microbiome of a companion animal, e.g., a domestic dog.

Definitions

The terms used in this specification generally have their ordinary meanings in the art, within the context of the present disclosure and in the specific context where each term is used. Certain terms are discussed below, or elsewhere in the specification, to provide additional guidance to the practitioner in describing the methods and compositions of the present disclosure and how to make and use them.

Throughout the description and claims of this specification, the words "comprise" and "contain" and variations of the words, for example "comprising" and "comprises," mean "including but not limited to," and do not exclude other components, integers or steps. Moreover, the singular encompasses the plural unless the context otherwise requires. In particular, where the indefinite article is used, the specification is to be understood as contemplating plurality as well as singularity, unless the context requires otherwise.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "animal" as used in accordance with the present disclosure refers to a wide variety of animals, such as quadrupeds, primates, and other mammals. For example, the term "animal" can refer to domestic animals including, but not limited to, dogs, cats, horses, cows, ferrets, rabbits, pigs, rats, mice, gerbils, hamsters, goats, and the like. The term "animal" can also refer to wild animals including, but not limited to, bison, elk, deer, venison, duck, fowl, fish, and the like. In some embodiments, the animal is a companion animal. In certain instances, the animal is a dog or a cat.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value.

As used herein, the term "oral disease or disorder," refers to a disease or disorder that occurs in an oral cavity of a subject (e.g., an animal) and that is caused by or is associated with one or more bacteria. For example, the disease or disorder can affect the teeth or the gums of the subject. Exemplary oral diseases or disorders of the present disclosure include, but are not limited to, periodontal disease, gingival stomatitis, odontoclastic resorptive lesions, and oral malodor.

As used herein, the term "periodontal disease," also known as gum disease, refers to an inflammation or infection that affect the tissues surrounding the teeth. Periodontal disease can range in severity, e.g., from gingivitis (e.g., dental plaque-induced gingivitis) to periodontitis.

As used herein, and as is well-understood in the art, "treatment" refers to an approach for obtaining beneficial or desired results, including clinical results. For purposes of this subject matter, beneficial or desired clinical results include, but are not limited to, alleviation or amelioration of one or more symptoms, diminishment of extent of a disorder, stabilized (i.e., not worsening) state of a disorder, prevention of a disorder, delay or slowing of the progression of a disorder, and/or amelioration or palliation of a state of a disorder. The decrease can be an about 0.01%, about 0.1%, about 1%, about 5%, about 10%, about 20%, about 30%, about 40%, about 50%, about 60%, about 70%, about 80%, about 90%, about 95%, about 98% or about 99% decrease in severity of complications or symptoms. "Treatment" can also mean prolonging survival as compared to expected survival if not receiving treatment. The term "preventing," as used herein, means partially or completing treating before the disorder or condition occurs.

Preferred features of each aspect of the presently disclosed subject matter can be as described in connection with any of the other aspects. Within the scope of this application, it is expressly intended that the various aspects, embodiments, examples and alternatives set out in the preceding paragraphs, in the claims and/or in the following description and drawings, and in particular the individual features thereof, can be taken independently or in any combination. That is, all embodiments and/or features of any embodiment can be combined in any way and/or combination, unless such features are incompatible.

Bacteria in the Oral Microbiome

The present disclosure relates to, inter alia, kits and related methods for detecting one or more bacteria in an oral microbiome of an animal. The one or more bacteria can be associated with an oral disease or disorder, e.g., periodontal disease, or good oral health. The animal can be a companion animal, such as a dog or a cat.

In some embodiments, the one or more bacteria associated with periodontal disease can be Peptostreptococcaceae sp. In some embodiments, the one or more bacteria associated with periodontal disease is selected from the group consisting of *Peptostreptococcus* sp., *Synergistes* sp., *Clostridiales* sp., *Eubacterium nodatum*, *Selenomonas* sp., *Bacteroidetes* sp., *Odoribacter denticanis*, *Desulfomicrobium ovale*, *Moraxella* sp., *Bacteroides denticanoris*, *Fillifactor villosus*, *Porphyromonas canoris*, *Porphyromonas gulae*, *Treponema denticola*, or *Porphyromonas salivosa*. In certain embodiments, the one or more bacteria includes *Peptostreptococcus* sp., volatile organic compound producing bacteria, or both. In further embodiments, the one or more bacteria includes Peptostreptococcaceae XIII [G-1] sp., Peptostreptococcaceae COT-030, Peptostreptococcaceae COT-005/004, Peptostreptococcaceae COT-047, and/or Peptostreptococcaceae COT-019.

Bacterial community profiles within an oral microbiome of an animal can vary depending on the source of a sample taken from the animal. For example, three discrete oral niches can include soft tissue surfaces, such as the lip, cheek, and tongue; hard tissue surfaces, such as the teeth; and saliva. In some embodiments, the oral niche is from a hard tissue surface, such as one or more teeth. In some embodiments, the oral niche includes the gingival margin or supragingival surface. The methods and kits of the disclosed subject matter can be used to detect bacteria in the oral microbiome of a wide variety of animals, such as quadrupeds, primates, and other mammals. The methods and kits of the disclosed subject matter are particularly well suited for use with companion animals, such as dogs, cats, and other domesticated animals.

Kits for Testing the Oral Microbiome

The present disclosure provides kits that are useful for testing the oral microbiome of an animal. The kits can be used to collect a sample in which one or more bacteria associated with an oral disease or disorder (e.g., periodontal disease) or good oral health are detected. As disclosed herein, a kit for testing the oral microbiome of an animal generally includes, amongst other things, a sample collection device having a handle and a head opposite the handle. The kit further includes a dry container for storing the sample collection device. The container has an open position for receiving at least a portion of the head and a closed position. The dry container also defines an aperture to permit communication between an inside of the dry container with an external environment The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of the kit in accordance with the disclosed subject matter are shown in FIGS. 1A-2B.

For purpose of illustration and not limitation, reference is made to the exemplary embodiment of a sample collection device 100 shown in FIG. 1A. The sample collection device 100 generally includes a handle 101 and a head 102 opposite the handle. The head 102 can include a first end 104 proximate the handle 101 and a second end 105 distal to the handle defining a longitudinal axis therebetween. The handle 101 can also include a first end 111 and a second end 112 proximate the first end 104 of the head with a longitudinal axis defined therebetween. With reference to the exemplary embodiment of a sample collection device 110 depicted in FIG. 1B, the longitudinal axis of the head 102 can be disposed at an angle 103 with respect to the longitudinal axis of the handle 101. For purpose of example and not limitation, the angle 103 can be between about 90 degrees to about 170 degrees. As embodied herein, the angle 103 can be an obtuse angle.

The handle 101 and the head 102 can each be any suitable shape, such as rectangular or cylindrical. For purpose of example and not limitation, and as embodied herein, the handle 101 can have a generally cylindrical shape and the head 102 can have a generally conical shape. The head 102 of the collection device can be any appropriate size for the animal on which it is to be used. For purpose of example and not limitation, the head can be between approximately 1.5 cm and approximately 2.5 cm in length, particularly between approximately 1.7 cm and approximately 2.3 cm in length, especially between approximately 2 cm and approximately 2.1 cm in length as measured along the longitudinal axis of the head 102. The handle 102 can also be any suitable dimension depending on the animal on which the sample collection device is to be used. The outer surface of the juncture of the head and the handle can be rounded forming a convex surface.

The handle 101 can be made of any suitable material. For purpose of example, and as embodied herein, the handle 101 can be made of a rigid plastic material. The handle 101 can have any suitable length or diameter. The length of the handle 101 can be selected such that a user can comfortably grip the handle and reach the rear portions of the mouth of the animal to be swabbed. For purpose of example and not limitation, and as embodied herein, the diameter of the handle 101 can be between approximately 1.5 mm and approximately 7 mm. The outer surface of the handle 101 can be substantially smooth. Additionally or alternatively, portions of the handle 101 can be textured to improve the grip.

The head 102 can be made of any suitable material for sample collection. For purpose of example and not limitation, the head can be a swab, cotton, foam, nylon, polyester, rayon, and combinations thereof. Additionally or alternatively, and as embodied herein, the head can include bristles. The bristles can be made of any of the materials referenced above. For purpose of example, and as embodied herein, the bristles can be made of nylon. As discussed further herein, the bristles can be configured to capture sample therebetween.

The bristles can be arranged in any appropriate pattern on the surface of the head. For purpose of example and not limitation, the bristles can cover all or part of the surface of the head. For example, where the head is cylindrical, the bristles can be positioned over, for example, at least about 50%, at least about 60%, at least about 70% or at least about 80% of the surface of the head. For example, and with reference to FIG. 1D, when viewing head 102 in front view along the longitudinal axis of the head, the bristles 108 can cover about 90 degrees, about 135 degrees, about 180 degrees, about 225 degrees, about 270 degrees, about 315 degrees or about 360 degrees of the outer surface of the head.

The bristles on the head 102 can be any suitable length. With reference to the partial detail view of head 102 depicted in FIG. 1C, a length dimension 107 can be measured from a central longitudinal axis of the head 102 to the end of each bristle 108. For purpose of example, and not limitation, the length dimension of the bristles on one side of the head can be between approximately 1.5 mm and 5 mm depending on the application of the sample collection device and the animal from which a sample is to be collected. The bristles on the head 102 can be of substantially similar length dimension. Additionally or alternatively, the bristles can be of different lengths. For purpose of example, and as embodied herein, the bristles 108 at a first end 104 of the head 102 proximate the handle 101 can be longer than bristles 108 at a second end 105 of the head 102 distal to the handle 101. As further embodied herein, the bristle length dimension can taper from the first end 104 to the second end 105 of the head 102 to define a substantially conical shape. For purpose of example and not limitation, and as further embodied herein, the bristles 108 can be arranged together to define rings extending around the circumference of the head 102. Additionally, or alternatively, the bristles 108 can be arranged in a spiral like pattern extending around the circumference of the head 102 and extending from the first end 104 of the head 102 to the second end 105 of the head 102.

For purpose of illustration and not limitation, reference is made to the exemplary embodiment of a dry container 200 shown in FIGS. 2A and 2B (not drawn to scale). The dry container 200 can be configured to house the sample collection device 100 of FIG. 1A. The container 200 is generally used for storing the sample collection device 100. With reference to FIG. 2A, the container has an open position for receiving at least a portion of the sample collection device 100. With reference to FIG. 2B, the container has a closed position to wholly house the device 100 therein. As shown in FIG. 2A-2B, the container can comprise a bottom segment 210 and a top segment 220. The bottom segment and top segment can be coupled together by snap fit, threaded connection, or other connections known in the art. Additionally, or alternatively, the first section 201 and second section 202 can be hingedly attached or connected by other suitable connection. Additionally or alternatively, container 200 can be formed from a unitary piece with an openable slot to receive the device therein.

The dry container can further define at least one aperture 205 to permit communication between an inside of the dry container with an external environment. As described further herein, the at least one aperture creates an opening to the external environment to allow a sample collected on the sample collection device to continue air drying while the sample is stored in the dry container 200, which can be beneficial for sample stability. The at least one aperture 205 can be disposed at any suitable location on the dry container 200 to facilitate a head 102 of the device therein being exposed to ambient air for drying purposes. FIG. 2C depicts an example of a container 200 in the closed position with a plurality of apertures disposed at a top of the tog segment 220. In such configuration, a sample collection device having a sample thereon can be adequately stored in the dry container upon swabbing of an animal, while having the head of the device being adjacent to the plurality of apertures for drying. In an alternate embodiment, the container does not include at least one aperture and instead includes a moisture absorbing device therein to absorb moisture within the container and allow for the drying of a sample collection device. Such moisture absorbing device can be any device as known in the industry, such as but not limited to, silica gel. It is furthermore contemplated that the embodiment having a dry container with at least one aperture can further include a moisture absorbing device to further assist in removing moisture from within the container and in assisting with drying the sample collection device stored therein. The dry container of FIG. 2C includes a flat bottom such that the dry container can stand upright as shown.

FIG. 2D depicts another embodiment of the dry container 200 further including a balancing stand 250. The stand 250 can be monolithic with the dry container 200. Alternatively, the stand 250 can be a separate component attachable with the dry container 200. As shown, the stand can provide additional stability to the dry container 200 to permit a sample collection device 200 to rest within the dry container while air drying. As such, the device 100 can air dry within the container 200 while in the open position, or alternatively the device 100 can air dry within the container 200 while in the closed position.

The container 200 can be made of any suitable material. For purpose of example, and as embodied herein, the container 200 can be made of a plastic material. As embodied herein, the container 200 can receive the entire sample collection device 100 therein. Additionally, or alternatively, the container can receive at least a portion of the head 102. The dry container used to store the sample collection device after collection of a sample can be the same container used to supply the sample collection device. The dry container can be sterilized using traditional packaging sterilization methods. While the dry container embodied herein has a plastic construction, it is to be understood that containers constructed of other suitable materials can be used in accordance with the disclosed subject matter.

Figure 2E:
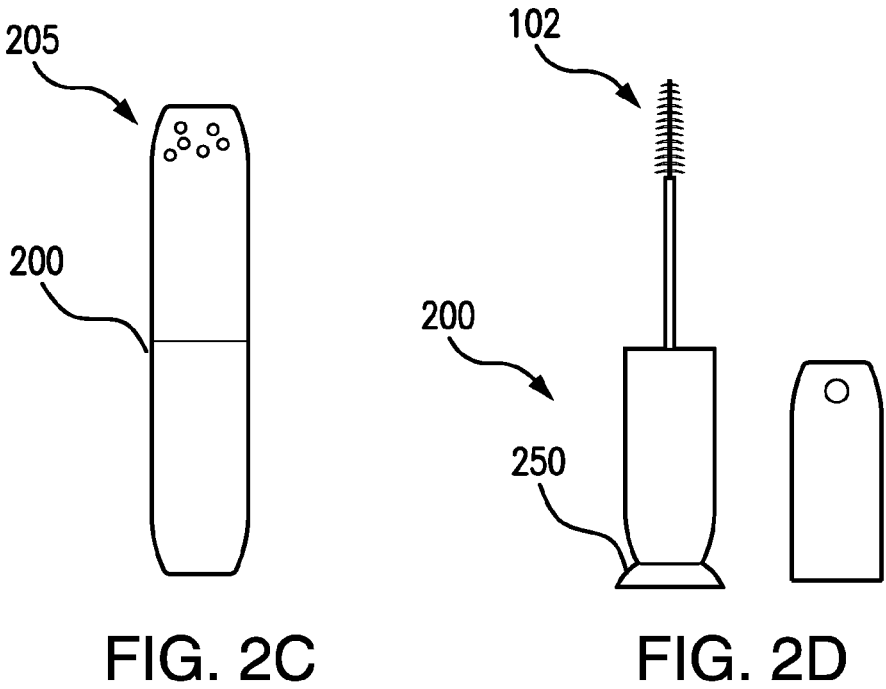
FIG. 2E is a front view of mailing package according to the disclosed subject matter.
Figure 2E:
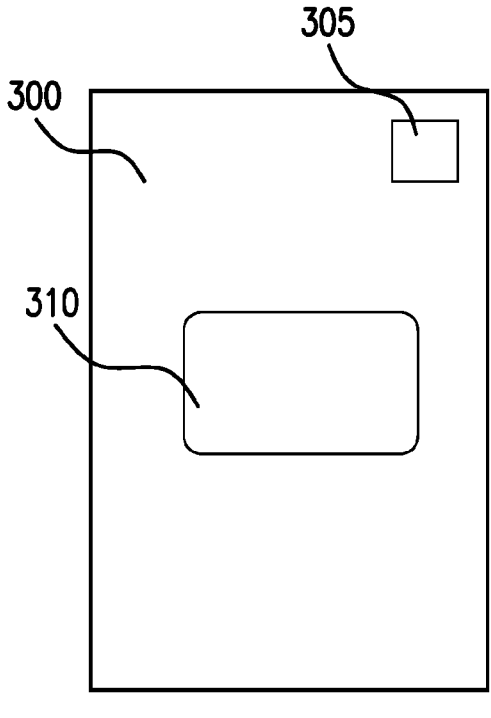

As shown in FIG. 2E, the kit can further include an envelope or sleeve 300 to receive the container with the device therein. The envelope can be used for storing the dry container with the device 100 therein and include an appropriate label identifying the animal that the sample has been collected from. The envelope can later be accessed to obtain the dry container with device therein for further testing of the device. Additionally or alternatively, the envelope can further include pre-paid postage 305 and a pre-addressed label 310 for easy shipment of the sample collection device and container to a lab facility if such facility is not present at the sample collection location. The lab facility can further test the sample as further described herein. For purpose of example, the envelopes or sleeves can be constructed of paper, plastic, foil, or any further suitable material that is non-interactive with the contents inside.

Methods for Testing the Oral Microbiome

Methods of using the kits disclosed above are provided herein. The disclosed methods include, e.g., collecting a sample and detecting one or more bacteria in the sample, as well as monitoring the oral health of an animal by using the presently disclosed kits. In any of the disclosed methods, the sample can be a plaque sample. In any of the disclosed methods, the animal can be a companion animal, such as a dog or a cat.

An exemplary method of the present disclosure includes a method of collecting a sample from an oral cavity of an animal. The method of collecting a sample from an oral cavity of an animal includes: providing a kit as disclosed herein, which includes a sample collection device having a handle and a head opposite the handle and a dry container for storing the sample collection device, the container having an open position for receiving at least a portion of the head and a closed position and defining an aperture to permit communication between an inside of the dry container with an external environment; swabbing a mouth of the animal with the sample collection device to collect the sample; and drying the head and storing the sample collection device for a time t1. The method can also include performing an assay on the sample to measure an amount of a microbial nucleic acid to detect and/or to measure an amount of one or more bacteria (e.g., a bacterium found in the oral microbiome of an animal) in the sample.

The present disclosure also features a method of detecting one or more bacteria in an oral microbiome of an animal. The method of detecting one or more bacteria in an oral microbiome of an animal includes: providing a kit as disclosed herein, which includes a sample collection device having a handle and a head opposite the handle and a dry container for storing the sample collection device, the container having an open position for receiving at least a portion of the head and a closed position, wherein the dry container defines an aperture to permit communication between an inside of the dry container with an external environment; swabbing the mouth of the animal with the sample collection device to collect a sample; drying the head and storing the sample collection device for a time t1; and performing an assay on the sample to measure an amount of a microbial nucleic acid to detect the one or more bacteria and/or to measure an amount of the one or more bacteria in the sample.

Another exemplary method of the present disclosure includes a method of monitoring an oral health of an animal, which includes: providing a first kit and a second kit as disclosed herein, each of the first and second kit including a sample collection device having a handle and a head opposite the handle and a dry container for storing the sample collection device, the container having an open position for receiving at least a portion of the head and a closed position, wherein the dry container defines an aperture to permit communication between an inside of the dry container with an external environment; swabbing the mouth of the animal with the sample collection device of the first kit to collect a first sample at a first time and swabbing the mouth of the animal with the sample collection device of the second kit to collect a second sample at a second time; drying the head and storing the sample collection device for a time t1; testing the first sample to detect a first amount of one or more bacteria and testing the second sample to detect a second amount of one or more bacteria, wherein the one or more bacteria includes bacteria associated with an oral disease or disorder (e.g., periodontal disease), bacteria associated with good oral health, or both; and comparing the first amount with the second amount to determine a difference between the first amount and the second amount.

Another disclosed method includes a method of treating or preventing an oral disease or disorder in an animal in need thereof, wherein the method includes: providing a kit including a sample collection device having a handle and a head opposite the handle and a dry container for storing the sample collection device, the container having an open position for receiving at least a portion of the head and a closed position, wherein the dry container defines an aperture to permit communication between an inside of the dry container with an external environment; diagnosing the animal with the oral disease or disorder and/or determining the likelihood of the animal developing the oral disease or disorder by: swabbing the mouth of the animal with the sample collection device to collect a sample; drying the head and storing the sample collection device for a time t1; and performing an assay on the sample to measure an amount of a microbial nucleic acid to detect and/or to measure an amount of one or more bacteria indicative of the oral disease or disorder (e.g., periodontal disease), or is indicative of poor or worsening oral health; and treating or preventing the oral disease or disorder in the animal by recommending a change in oral hygiene or an intervention.

Furthermore, the present disclosure also features a method of treating or preventing an oral disease or disorder in an animal in need thereof, the method comprising: providing a first kit and a second kit, each of the first and second kit including a sample collection device having a handle and a head opposite the handle; and a dry container for storing the sample collection device, the container having an open position for receiving at least a portion of the head and a closed position, wherein the dry container defines an aperture to permit communication between an inside of the dry container with an external environment; diagnosing the animal with the oral disease or disorder and/or determining the likelihood of the animal developing an the oral disease or disorder by swabbing the mouth of the animal with the sample collection device of the first kit to collect a first sample at a first time and swabbing the mouth of the animal with the sample collection device of the second kit to collect a second sample at a second time; drying the head and storing the sample collection device for a time t1; testing the first sample to detect a first amount of one or more bacteria and testing the second sample to detect a second amount of one or more bacteria, wherein the one or more bacteria includes bacteria associated with the oral disease or disorder (e.g., periodontal disease), bacteria associated with good oral health, or both; and comparing the first amount with the second amount to determine a difference between the first amount and the second amount, wherein the difference between the first amount and the second amount is indicative of the oral disease or disorder, or is indicative of poor or worsening oral health; and treating or preventing the oral disease or disorder in the animal by recommending a change in oral hygiene or an intervention.

According to the present disclosure, any of the methods can include providing a kit as disclosed herein, i.e., having a sample collection device 100 and a dry container 200. The sample collection device and container of the kit can have any of the various features described herein. The disclosed methods further include swabbing the mouth of an animal with the sample collection device 100 to collect a sample. The disclosed methods further include drying the head 102 and storing the sample collection device 100 in the dry container 200.

The sample collection device 100 can be dried using any suitable technique. For purpose of example and as embodied herein, the sample collection device 100 can be air dried. For purpose of example and not limitation, the sample collection device 100 can be air dried at room temperature.

Swabbing the mouth of the animal with the sample collection device 100 can be performed using any suitable technique known in the art. For purpose of example and not limitation, the step of swabbing the mouth of the animal can include brushing or swabbing at least one of the gums, the gum-line, the teeth, the tongue, cheek, the roof of the mouth, and/or other part of the oral cavity. The step of swabbing can include slow rotation of the swab to coat the bristles 109 along the head 102 with the sample such that the sample stays contained on the bristles. The rotation speed of the swab can be controlled to prevent sample from flicking off from or being slung from the bristles 109. In some embodiments, the swabbing includes swabbing the gums, the gum-line, and/or the teeth. The swabbing step can be used to collect a plaque sample from the oral cavity of the animal.

According to the methods disclosed herein, detecting a presence or absence and an amount of one or more bacteria associated with an oral disease or disorder can be indicative of poor or worsening oral health. For example, the amount of the one or more bacteria detected can be compared against a control dataset that provides the healthy range of amounts of the same bacteria in healthy animals of the same species. It can be determined that if the amount of the one or more bacteria detected is lower than the healthy amount in the control dataset, and/or if the amount of the one or more bacteria detected is greater than the healthy amount in the control data, the amount of said bacteria can be indicative of poor or worsening oral health in the animal. For example, in certain embodiments, when one sample is collected from the animal, the amount of the one or more bacteria detected in the sample is compared against the control dataset to determine if the one or more bacteria is indicative of poor or worsening oral health in the animal.

Any one of the methods disclosed herein can additionally include further detecting a presence of a fungus, a virus, and/or other microorganisms in the oral microbiome of the animal.

As discussed above, methods of monitoring the oral health of an animal are also provided. The disclosed methods include providing a first kit and a second kit, each having a sample collection device 100 and a dry container 200. The disclosed methods can further include providing a third or further subsequent kits, each having a sample collection device 100 and a dry container 200. The sample collection device and container of each kit can have any of the various features described herein. The sample collection device and container of each kit can have substantially the same features, or substantially different features. The disclosed methods further include swabbing the mouth of an animal with the sample collection device 100 to collect a first sample and swabbing the mouth of the animal with a sample collection device to collect a second sample at a second time. Swabbing the mouth of the animal can be done using any of the methods described herein.

The disclosed methods further include testing the first sample and the second sample for the presence or absence and amount of one or more bacteria associated with an oral disease or disorder, bacteria associated with good oral health, or both. Bacterial species associated with an oral disease or disorder are known in the art or disclosed herein. The disclosed methods further include comparing a first amount of bacteria associated with an oral disease or disorder, bacteria associated with good oral health, or both in the first sample with a second amount of bacteria associated with an oral disease or disorder, bacteria associated with good oral health, or both in the second sample to determine a difference between the first amount and the second amount. Additionally, the disclosed methods can include taking multiple samples and determining a difference by comparing a sample against a consensus built up from at least two samples.

An increase in the presence of bacteria or other markers associated with an oral disease or disorder (e.g., periodontal disease) and/or a decrease in the presence of bacteria or other markers associated with good oral health in the second sample when compared to the first can be indicative of poor or worsening oral health. A decrease in the presence of bacteria or other markers associated with an oral disease or disorder (e.g., periodontal disease) and/or an increase in the presence of bacteria or other markers associated with good oral health in the second sample when compared to the first can be indicative of improving oral health.

The methods disclosed herein can further include providing a third kit and testing a third sample and comparing the third sample to the second or first sample or any previous sample. The method can also further include providing further subsequent kits and testing any subsequent sample and comparing them to the third, second, or first sample or any other previous sample. As previously described, the relative increase or decrease of bacteria or other markers associated with oral health can be indicative of improving or poor or worsening oral health, respectively.

According to any of the methods disclosed herein, the method can also include the step of recommending a change in oral hygiene or an intervention, in the event that a sample or a change in samples is indicative of poor or worsening oral health. Such an intervention can include, for example, cleaning the mouth of the animal (such as by tooth brushing), removing plaque from the mouth of the animal, performing a gingivectomy, removing one or more diseased teeth from the mouth of the animal, administering an antibiotic, an anti-inflammatory drug, and/or an analgesic to treat an oral infection, providing dental chews to the animal or increasing frequency of dental chews, introducing or increasing frequency of non-edible chewing toys and dispensers, introducing or increasing frequency of tooth brushing, increasing use of dental diets (e.g., a diet for improving dental health), a professional cleaning and/or polishing the teeth by a veterinarian, scaling the teeth to remove tartar or calculus, providing a dental treatment solution in water, or any combination thereof. In alternative embodiments of any one of the methods disclosed herein, the method includes recommending no change to the oral care routine of the animal.

Additionally, or alternatively, any of the presently disclosed methods can include diagnosing the likelihood of an animal having an oral disease or disorder based on the presence or absence and amount of one or more bacteria associated with the oral disease or disorder and/or good oral health. For example, the presence of one or more bacteria associated with an oral disease or disorder can increase the likelihood of the animal having the oral disease or disorder. On the other hand, absence of one or more bacteria associated with an oral disease or disorder can decrease the likelihood of the animal having the oral disease or disorder. The oral disease or disorder can be, for instance, periodontal disease, gingival stomatitis, odontoclastic resorptive lesions, and/or oral malodor. Additionally, or alternatively, any of the presently disclosed methods can include diagnosing the likelihood of an animal having a disease or disorder related to poor oral health, such as a heart or kidney disease, based on the presence or absence and amount of one or more bacteria associated with the oral disease or disorder and/or good oral health.

Storage Conditions

Any of the disclosed methods of using the kits of the disclosed subject matter can include storing the sample collection device for transfer and analysis in the dry container. As an ordinary skilled artisan would recognize, biological samples taken from a subject (such as an animal) containing DNA are typically stored in a buffer solution. The buffer solution usually acts as a preservative, halts any further bacterial growth, and/or helps to maintain the integrity of the DNA, e.g., by inactivating any deoxyribonucleases that can be present in the sample and preventing DNA degradation. Buffer can also help to preserve DNA integrity during ambient temperature fluctuations that can affect DNA stability under certain conditions. However, according to the present disclosure, the sample collection device containing the DNA sample is in fact advantageously stored in the dry container without any buffer.

As further discussed below in Example 1, it was surprisingly found that assays for determining the DNA content of the sample were still successfully performed without any adverse effect due to the storage without buffer, and dry storage was found to be the best storage condition out of those tested. Dry storage can be particularly advantageous to the presently disclosed methods due to ease of maintenance of the sample as well as ease of use of the kit, ease of transportation of the sample, and lower costs.

For purpose of example, and as embodied herein, the sample collection device 100 can be stored in the container 200 in the open condition or the closed condition. For purpose of example and not limitation, the sample collection device can be stored in the container 200 at a range of suitable temperatures disclosed herein.

For instance, the sample collection device can be stored in the container 200 at room temperature (about 20° C.). In further non-limiting examples, the sample collection device can be stored at a temperature of up to about 40° C., including about 20° C., about 25° C., about 30° C., about 35° C., or about 40° C. In other non-limiting examples, the sample collection device can be stored at a temperature of from about 20° C. to about 40° C., or from about 20° C. to about 25° C., or from about 25° C. to about 30° C., or from about 30° C. to about 35° C., or from about 35° C. to about 40° C., or from about 25° C. to about 35° C., or from about 30° C. to about 40° C., or from about 20° C. to about 35° C., or from about 25° C. to about 40° C. In some embodiments, the sample collection device is stored at a temperature of up to about 40° C. In other embodiments, the sample collection device is stored at a temperature of from about 20° C. to about 40° C.

Additionally, the sample collection device can be stored in the dry container for a time period referred to herein as t1.

The time period t1 for which the sample collection device is stored can be, for example, up to about 30 minutes, about 1 hour, about 6 hours, about 12 hours, about 1 day, about 2 days, about 3 days, about 4 days, about 5 days, about 6 days, about 7 days, about 8 days, about 9 days, about 10 days, about 11 days, about 12 days, about 13 days, or about 14 days following collection of the sample. In some embodiments, the sample collection device is stored in the dry container for a time period of up to about 14 days, such as for purposes of example from about 5 days to about 14 days.

Assays for Detecting Bacteria

The disclosed methods of using the kits of the disclosed subject matter can include performing an assay on the sample to measure an amount of a microbial nucleic acid. The microbial nucleic acid can be a microbial DNA or RNA, e.g., a 16S ribosomal DNA (rDNA) or 16S ribosomal RNA (rRNA). In some embodiments, the disclosed methods include further measuring a host nucleic acid (e.g., DNA or RNA) in addition to the microbial nucleic acid. Detecting the host nucleic acid can be useful, for instance, in predicting future risk of periodontal disease or possibility of other genetic conditions that can be a co-morbidity for periodontal disease. Various assays for identifying the presence of bacteria or other markers associated with an oral disease or disorder (e.g., periodontal disease) or good oral health are known in the art, such as quantitative polymerase chain reaction (qPCR) assays. The appropriate methods for performing such an assay can be ascertained by one of ordinary skill in the art.

For purpose of example, any of the disclosed methods can include performing an assay for testing for the presence and/or relative amounts of any bacteria disclosed herein, such as, but not limited to, Peptostreptococcaceae sp. and/or volatile organic compound producing bacteria, or any other periodontal bacterium as commonly known with oral health, such as but not limited to *Peptostreptococcus* sp., *Synergistes* sp., *Clostridiales* sp., *Eubacterium nodatum, Selenomonas* sp., *Bacteroidetes* sp., *Odoribacter denticanis, Desulfomicrobium ovale, Moraxella* sp., *Bacteroides denticanoris, Fillifactor villosus, Porphyromonas canoris, Porphyromonas gulae, Treponema denticola,* or *Porphyromonas salivosa.* According to the present disclosure, in some embodiments, the bacteria is Peptostreptococcaceae XIII [G-1] sp.

Additionally or alternatively, any of the disclosed methods can include performing a universal qPCR assay (UniB) which detects for the presence of bacterial DNA in the dog oral microbiome. Universal primers such as those of UniB are known to skilled people in the art and examples include those described in Ott et al., *J. Clin. Microbiol.* 2004 June; 42(6): 2566-2572. doi: 10.1128/JCM.42.6.2566-2572.2004, the contents of which is incorporated by reference in its entirety. Methods for performing qPCR assays are known in the art.

The methods can also include a step of extracting a nucleic acid, e.g., performing a DNA extraction, according to methods known to an ordinary skilled artisan in the art prior to performing the qPCR assay. Generally, a DNA extraction can be performed by lysing the cells containing the DNA and precipitating and purifying out the DNA.

As disclosed herein, one non-limiting example of a procedure for testing for the presence or absence and amount of a bacteria in a sample includes using a Masterpure™ Gram positive DNA purification kit, optionally including the addition of an overnight lysis (EpiCentre, catalogue # MGP04100). In a non-limiting example, DNA-containing samples are centrifuged at 5000×g for 10 minutes, and the bacterial pellet is re-suspended in 150 μL TE buffer by vortexing. Ready-Lyse™ Lysozyme Solution (1 μL; Epicentre, catalogue #R1804M) is added to the bacterial suspension, which is then incubated at 37° C. for 18 hours. Following DNA extraction, the DNA pellet is re-suspended in TE buffer (10 mM Tris HCl and 0.5 mM pH 9.0 EDTA). The quantity of DNA can then be determined using a Qubit® dsDNA High Sensitivity Assay Kit (Thermo Fisher Scientific, Inc.). However, other appropriate methods of testing for the presence or absence and amount of a bacteria in a sample can be ascertained by one of ordinary skill in the art, and are not limited by the present disclosure or following Examples.

Additionally or alternatively, any of the disclosed methods can include detecting bacteria by testing the sample for a presence of bacteria. For purpose of example and not limitation, testing the sample for the presence of bacteria can include testing the sample for the presence and/or amount of one or more of the bacteria disclosed herein, e.g., bacteria associated with an oral disease or disorder (e.g., periodontal disease), bacteria associated with good oral health, or both. Detecting a presence of one or more of the bacteria disclosed herein can, for instance, indicate that the animal has or is susceptible to developing an oral disease or disorder Additionally or alternatively, any of the disclosed methods can include detecting bacteria by testing the sample for an absence of bacteria. For purpose of example and not limitation, testing the sample for the absence of bacteria can include testing the sample for the absence of one or more of the bacteria disclosed herein, e.g., bacteria associated with an oral disease or disorder (e.g., periodontal disease). Detecting the absence of the one or more of the bacteria associated with the oral disease or disorder can, for instance, indicate that the animal does not have an oral disease or disorder or is less likely to develop an oral disease or disorder.

Additionally or alternatively, the disclosed methods of using the kits of the disclosed subject matter can include testing the sample for the presence and/or relative amounts of microbes associated with oral health, especially bacteria, can include testing for the presence and/or relative amounts of a bacterial nucleic acid (e.g., DNA or RNA); performing biochemical analysis; enzyme tests; or identifying any other biomarkers. For purpose of example and not limitation, the amount of microbes can be detected by detecting the amount of the bacterial nucleic acid (e.g., DNA or RNA), amount of biochemicals, enzymes or other biomarkers present in a sample.

In any of the methods disclosed herein, the detection of the presence of bacteria or other markers can include measuring the amounts of bacteria or other markers, and the amounts can be compared to a scale that correlates the amounts of bacteria or other markers to the likelihood that the animal has oral disease or disorder (e.g., periodontal disease) or poor oral health. The likelihood can be indicated as a percentage. For purpose of example and not limitation, the Cq score of a qPCR test that detects the nucleic acid (e.g., DNA or RNA) of bacteria associated with oral disease or disorder (e.g., periodontal disease) can be used to create the scale for calculating the likelihood that the animal has oral disease or disorder (e.g., periodontal disease). A lower Cq score can indicate the presence of higher levels of the bacteria associated with oral disease or disorder (e.g., periodontal disease) and therefore the likelihood that the animal has oral disease or disorder (e.g., periodontal disease) can be higher than an animal with a higher Cq score.

For purpose of example and not limitation, a report can be generated summarizing the results of sample testing. In certain non-limiting embodiments, electronic communications can be used to communicate the report. For example, a personalized report can be generated and sent to communicate the animal's oral health status. In other embodiments, the report can be provided as a hard copy. The personalized report can, for example, include an indicator system such as a traffic light system, e.g., green, yellow, red, to communicate the oral health status of the animal. The personalized report can also include a representation of the scale as referenced above and an indication of where the animal's oral health falls on the scale.

The kits, methods and devices of the disclosed subject matter have demonstrated desired performance characteristics not achieved by conventional techniques to assess oral health in animals. For example, kits in accordance with the disclosed subject matter can be used to test the oral microbiome of an animal without the need for general anesthetic.

EXAMPLES

For purpose of understanding and not limitation, the presently disclosed subject matter will be better understood by reference to the following Examples, which are provided as exemplary of the disclosed subject matter, and not by way of limitation.

Example 1

Methods for Collecting Bacterial Samples from the Oral Microbiome of Canines This example discloses methods of collecting bacterial samples from the oral microbiome of canines with varying sample collection devices and storage conditions for storing the sample.

Methods

Study Cohort

The study cohorts comprised 30 and 31 Adult Labrador retrievers housed at the facility for study 1 (to assess sample collection devices) and study 2 (to assess transport options for sample collection devices) respectively. Dogs were aged between 2.6 and 9.4 years.

Sample Collection

Gingival margin plaque samples were collected by sweeping sample collection devices along the gumline on the outer buccal surface of teeth (canine (04), $1^{st}$, $2^{nd}$, $3^{rd}$ & $4^{th}$ premolars (05-08) and first molar (09)) (upper and lower) from one half of the mouth. For study 1, plaque was collected using the sample collection devices listed in Table 1 and each dog received plaque collections using two different sample collection devices, either A and B, C and D or E and F. For study 1, sample collection devices were placed in empty 1.5 mL microfuge tubes, claw clipped and later filled with 1.5 mL Tris EDTA buffer ("TE buffer") once all the samples had been collected on each day of the trial. For study 2, the nylon CytoSoft™ cytology brush (A in Table 1) was used for all plaque collections. The study 2 sample collection devices were removed from the vicinity of the dogs and sample collectors and placed into a 1.5 mL microfuge tube containing one of the buffers listed in Table 2. The TE buffer controls were frozen at –80° C. and the remaining sample collection devices were kept at room temperature for 5 days then the DNA extracted from the samples as described below.

TABLE 1

Sample collection device types and associated suppliers for devices tested in study 1.

| | Swab Type | Supplier | Product Code |
|---|---|---|---|
| A | CytoSoft ™ cytology brush (Nylon) | Medical Packaging Corporation | CYB-1 |
| B | Cotton swab, wood shaft (Dryswab ™) | Medical Wire & Equipment (MWE) Co Ltd | MW1048 |
| C | Foam swab, plastic shaft | Medical Wire & Equipment (MWE) Co Ltd | MW941 |
| D | Dacron bud, plastic shaft swab (Dryswab ™ Standard Polyester) | Medical Wire & Equipment (MWE) Co Ltd | MW1028D |
| E | PurFlock ® ultra swab | Medical Wire & Equipment (MWE) Co Ltd | MW830 |
| F | Rayon swab, plastic shaft | Sterilab Services | 155C |

TABLE 2

Buffer types tested in study 2.

| | Buffer Type | Supplier |
|---|---|---|
| A | Tris-EDTA[1] (Control) | |
| B | Dry/No buffer[2] | N/A |
| C | Amies transport media[2] | Thermo Fisher Scientific (Oxoid ™) |
| D | RNA protect bacterial reagent[2] | Qiagen |
| E | Nucleic acid stabilising solution[2] | Omnigene |
| F | 0.2% chlorohexidine[2] | Sigma (100% solution) |

[1]denotes storage buffer samples frozen at –80° C.
[2]denotes storage buffer samples kept at room temperature. Sample collection devices were kept at the storage temperatures indicated for 5 days prior to DNA extraction.

DNA Extraction

DNA was extracted from the plaque samples using a Masterpure™ Gram positive DNA purification kit according to the manufacturer's instructions with the addition of an overnight lysis (sourced from EpiCentre, catalogue #MGP04100). Plaque samples were centrifuged at 5000×g for 10 minutes and the bacterial pellet resuspended in 150 μL TE buffer by vortexing. Ready-Lyse™ Lysozyme Solution (1 μL; sourced from Epicentre, catalogue #R1804M) was added to the bacterial suspension which was then incubated at 37° C. for 18 hours. Following DNA extraction, the DNA pellet was resuspended in TE buffer (10 mM Tris-Cl and 0.5 mM pH 9.0 EDTA). The quantity and purity of DNA was determined using a Nanodrop ND1000 spectrophotometer (manufactured by Thermo Fisher Scientific).

Quantitative PCR (qPCR) Analyses

Various qPCR assays were developed against the 16S rRNA gene of Peptostreptococcaceae XIII [G-1] sp. and a universal qPCR assay (UniB) which detects for the presence of bacterial DNA in the dog oral microbiome. Similar universal primers such as those of UniB are known to skilled people in the art and examples include those described in Ott et al., *J. Clin. Microbiol.* 2004 June, 42(6): 2566-2572, Doi: 10.1128/JCM.42.6.2566-2572.2004, the content of which is incorporated by reference in its entirety.

Each individual 10 μL quantitative PCR (qPCR) reaction contained: 5 μL Applied Biosystems Gene Expression Taqman MasterMix (manufactured by Applied Biosystems, USA), 0.5 μL 20× concentrated assay, 1 μL 1:10 dilution of DNA and 3.5 μL nuclease-free water. Each assay contained a final concentration of 900 nM of each primer and 250 nM of each qPCR probe per reaction. Experiments were performed in triplicate. Positive and negative controls, also included in triplicate, were the M13 purified amplicon of CN030 at 0.001 ng/μL and nuclease-free water, respectively. Data were collected on an AB7900 HT machine (manufactured by Applied Biosystems, USA) and analyzed using GenEx software (developed by MultiD, Sweden).

Peptostreptococcaceae sp. normalized to UniB relative to nothing was calculated by performing the following equation on the mean, efficiency corrected Cq value for each sample: $2^{-(mean\ COT030\ Cq\ value-mean\ UniB\ Cq\ value)}$. COT-030 refers to canine oral taxon 030, which is a bacterial species of the Peptostreptococcaceae XIII [G-1] genus.

Statistical Analysis

For different sample collection device types (study 1), and buffers (study 2), there were three measures analyzed: UniB Cq, Peptostreptococcaceae sp. normalized to UniB relative to nothing, and DNA concentration. UniB Cq and DNA concentration were analyzed using a linear model with log10 measure modelled against sample collection device type for each of the paired dog groups. COT030 relative to nothing had a number of observations marked as "ND" (not detected) or "Detected." These missing values were imputed as 0.9 times the minimum observed COT030 relative to nothing value and a "Tobit" censored linear model was used to model $\log_{10}$ (COT030 relative to nothing) vs. sample collection device type, or buffer, with the imputed values treated as left-censored observations.

From these models, means and 95% confidence intervals were estimated. Contrasts between each pair of sample collection device types, or buffers, were calculated along with comparison groups using Tukey's honest significance test ("HSD test").

As a secondary analysis, in order to compare sample collection device types and buffers that were tested with the same cohort of dogs, three separate models were built for each measure using the individual cohorts. For each of the three models, the same analysis methods previously described were used, except that a random effect for dog was included. Additionally, only 2 sample collection device types, or 2 buffer types, were compared. For each model, confidence intervals were calculated along with contrasts between sample collection devices.

All analyses were performed using R statistical software version 3.4.3 from the R Foundation, with the lme4, AER, lmec, multcomp and multcompView libraries.

Results

Study Cohort

Gingival margin plaque bacterial communities were sampled from a total of 30 and 31 dogs for study 1 and study 2 respectively. Dog size and age are putative risk factors for periodontitis and therefore sample associated metadata was also obtained (Table 3).

TABLE 3

Summary of metadata for sample cohorts, numbers shown are mean ± sd.

|  | Study 1 | Study 2 |
| --- | --- | --- |
| Age | 6.9 ± 1.5 years | 7.2 ± 1.5 years |
| Gender | 21 female, 9 male | 22 female, 9 male |
| Neutered status | 29 yes, 1 no | 30 yes, 1 no |
| Bodyweight | 27.3 ± 3.4 kg | 27.2 ± 3.2 kg |
| Breed | Labrador retriever | Labrador retriever |

Sample Collection Devices

A sample overview for each sample collection device type is summarized in Table 4. Of the 60 samples analyzed by qPCR, there were only four instances where quantitative data for the levels of UniB were not obtained. UniB was utilized as a primary measure since a recent health status for the cohort of dogs was unknown. There were three instances where UniB was not detected and one instance where UniB was detected but the technical replicates were variable and outside the pre-defined range. These data provide an initial indication that all sample collection device types tested are suitable candidates for the collection of supragingival plaque from dogs' mouths.

TABLE 4

Swab analysis overview.

|  | Swab | Total samples | No. of "Not detected" | No. of "Detected" |
| --- | --- | --- | --- | --- |
| A | Nylon/CytoSoft ™ cytology brush | 10 | 0 | 0 |
| B | Cotton swab | 10 | 1 | 1 |
| C | Foam swab | 10 | 0 | 0 |
| D | Dacron (Polyester) swab | 10 | 0 | 0 |
| E | PurFlock ® swab | 10 | 1 | 0 |
| F | Rayon swab | 10 | 1 | 0 |

"Not detected" indicates samples that were not amplified in the 40 cycles of the qPCR reaction or had "minor amplifications" classified as non-amplifications by the PCR instrument and confirmed by human checking. "Detected" indicates samples where the triplicate Cq values were not within 0.25 Cq of one another, but values were all within the limit of quantification range.

Figure 3A:
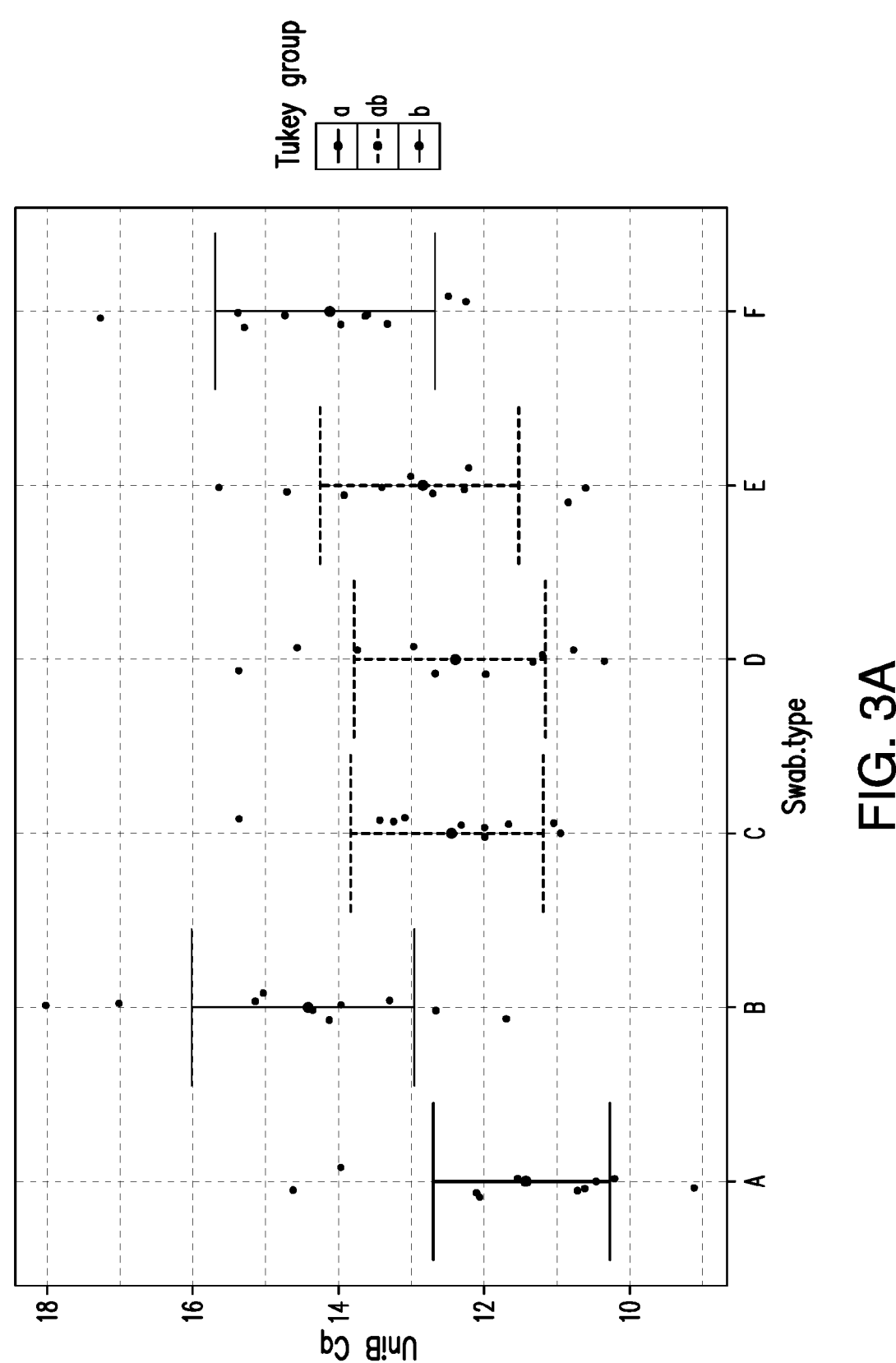
FIG. 3A is a graph depicting quantitation cycle (Cq) values marked by Tukey comparison group for UniB quantitative polymerase chain reaction (qPCR) assays of samples collected using exemplary sample collection device embodiments A-F as described in Example 1.
Figure 3B:
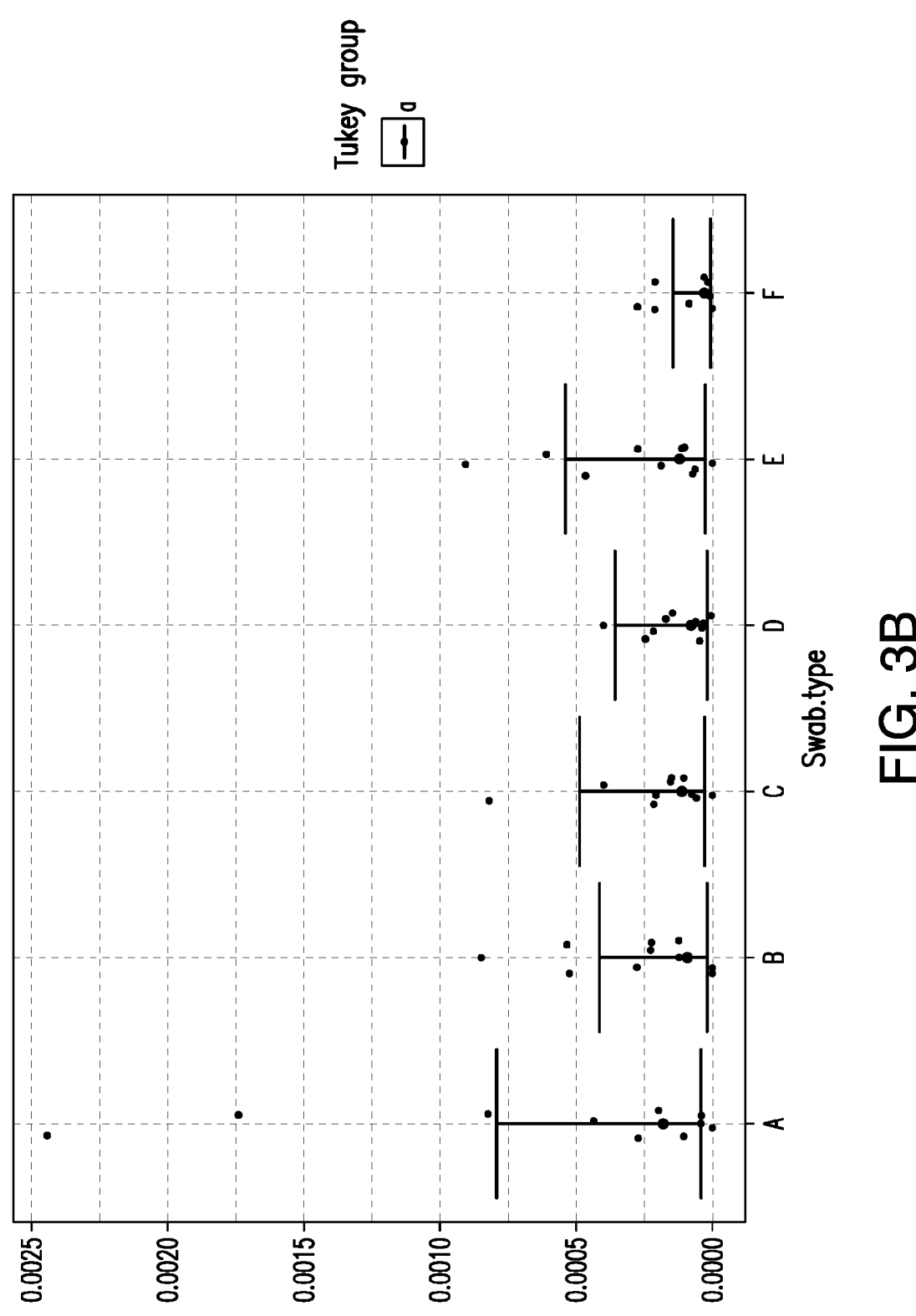
FIG. 3B is a graph depicting Cq values marked by Tukey comparison group for Peptostreptococcaceae sp. qPCR assays, normalized to UniB Cq relative to nothing, of samples collected using exemplary sample collection device embodiments A-F as described in Example 1.
Figure 3C:
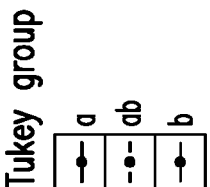
FIG. 3C is a graph depicting DNA concentration values measured by the Qubit marked by Tukey comparison group for samples collected using exemplary sample collection device embodiments A-F as described in Example 1.

The average Cq values and 95% confidence intervals for each sample collection device type for UniB and Peptostreptococcaceae sp. normalized to UniB relative to nothing qPCR assays, and DNA concentration measured using the Qubit are shown in FIG. 3A-FIG. 3C. The Qubit kit used was the dsDNA High Sensitivity (HS) assay (manufactured by Thermo Fisher Scientific Inc.) with a Qubit fluorometer (manufactured by Life Technologies, USA) with the manufacturer's dsDNA High Sensitivity (HS) assay (manufactured by Thermo Fisher Scientific Inc.). The Qubit data provides the calibration data to allow quantitation of the amount of DNA present in the other samples. Lower qPCR Cq values indicate higher bacterial levels. DNA concentration data can be used to understand how much DNA can be extracted from particular sample collection devices. For example, some devices can be good at collecting plaque, but there can be challenges associated with plaque removal in terms of laboratory processing. For the UniB qPCR assay, average Cq values were between 11 and 15 indicating relatively high total bacterial DNA concentrations as shown by FIG. 3A. The foam (Sample C), Dacron (Sample D) and PurFlock (Sample E) sample collection devices were assigned the same Tukey grouping and therefore did not significantly differ from any of the other three sample collection device types (p>0.05). The CytoSoft cytology brush (Sample A) significantly differed from the cotton (Sample B) and Rayon (Sample F) sample collection devices (p <0.05). The CytoSoft brush had the lowest Cq value for UniB, and the cotton and Rayon swabs the highest averages, indicating more bacterial DNA was harvested using the CytoSoft brush. With Peptostreptococcaceae sp. normalized to UniB, relative to nothing, all of the sample collection device types performed similarly with no significant differences observed for any of the comparisons as shown in FIG.

3B. All the sample collection device types delivered measurable concentrations of DNA using the Qubit as provided by FIG. 3C. The cytology, foam and Dacron sample collection devices delivered the highest DNA concentrations and were assigned to one statistical grouping. DNA concentrations from the cotton and PurFlock devices were lower but not significantly different from any of the other sample collection device types. The Rayon swab delivered the lowest average DNA concentration, significantly differing from the CytoSoft, foam and Dacron sample collection devices.

Technicians provided feedback from the procedure on ease of sampling, and the laboratory for ease of processing for the sample collection devices tested, as summarized in Table 5.

TABLE 5

Summary of results/insights gained from assessment of swabs.
Performance rating with respect to each parameter
indicated to be good, reasonable, and poor.

|   | Swab Type | Usability | Processing | UniB | DNA conc. |
|---|---|---|---|---|---|
| A | CytoSoft ™ cytology brushes (Nylon) | good | good | good | good |
| B | Cotton swab, wood shaft | good | poor | poor | poor |
| C | Foam swab, plastic shaft | reasonable | poor | reasonable | reasonable |
| D | Dacron bud, plastic shaft swab (Polyester) | reasonable | poor | reasonable | reasonable |
| E | PurFlock ultra swab | poor | poor | poor | reasonable |
| F | Rayon swab, plastic shaft | poor | poor | poor | reasonable |

Storage Buffers

To determine whether Peptostreptococcaceae sp. was stable under different storage conditions, it was first determined whether dogs in the study were positive for this organism. Analysis of the plaque samples collected as part of the sample collection device trial (study 1) using a qPCR assay for Peptostreptococcaceae sp. showed that all 31 dogs assessed were positive for this organism.

A descriptive overview for each storage condition is summarized in Table 6. The TE buffer stored at −80° C. represents the positive control. The numbers of "not detected" and "detected" for the qPCR assay for Peptostreptococcaceae sp. demonstrated that the storage buffers were roughly equal in performance, except for the Amies media and RNA protect bacterial reagent. For both of these storage buffers, more than 50% of the total samples failed to deliver quantitative qPCR results, with either "not detected" or "detected" results.

TABLE 6

Storage buffer sample analysis overview.

|   | Storage Buffer | Total samples | No. of "Not detected" | No. of "Detected" |
|---|---|---|---|---|
| A | TE | 11 | 2 | 0 |
| B | Dry (No buffer) | 11 | 1 | 2 |
| C | Amies transport media | 10 | 4 | 4 |
| D | RNA protect bacterial reagent | 10 | 3 | 3 |
| E | Nucleic acid stabilising solution (Omnigene) | 10 | 2 | 1 |
| F | 0.2% chlorohexidine | 10 | 2 | 1 |

"Not detected" indicates samples not amplified in the 40 cycles of the qPCR reaction or "minor amplifications" classified as non-amplifications by the PCR instrument and confirmed by human checking. "Detected" indicates samples where the triplicate Cq values were not within 0.25 Cq of one another but values were all within the limit of quantification range.

Figure 4A:
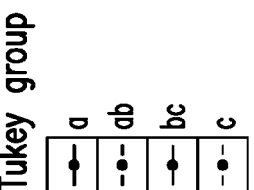
FIG. 4A is a graph depicting Cq values marked by Tukey comparison group for UniB qPCR assays of samples stored using exemplary storage conditions A-F as described in Example 1.
Figure 4B:
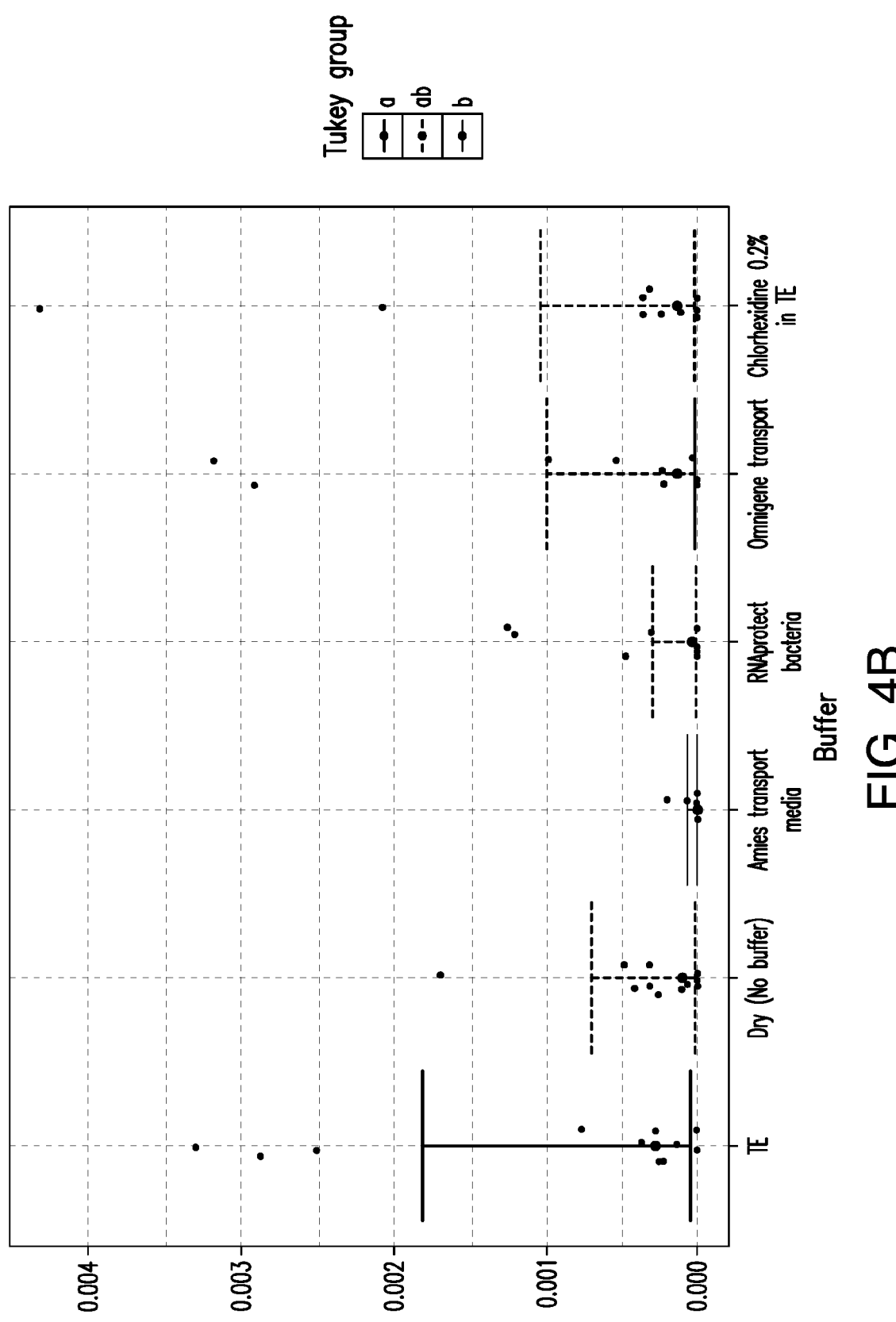
FIG. 4B is a graph depicting Cq values marked by Tukey comparison group for Peptostreptococcaceae sp. qPCR assays, normalized to UniB Cq relative to nothing, of samples stored using exemplary storage conditions A-F as described in Example 1.

The average Cq values and 95% confidence intervals for each storage condition for the universal bacterial primer (UniB) and Peptostreptococcaceae sp. qPCR assays, and DNA concentration measured using the Qubit are shown in FIG. 4A-FIG. 4B. The UniB Cq values delivered the most distinguishable results for the storage conditions, with the averages for all being within the acceptable range between 12.5 and 20 Cqs, as shown in FIG. 4A. The sample collection device that was dried and left at room temperature for 5 days delivered the lowest Cq values for UniB, indicating that this yielded the highest bacterial DNA concentration. The average Cq value for the dried sample collection device was not significantly different from the TE buffer control, which was immediately frozen and stored at −80° C. for 5 days (p>0.05). However, the three other storage conditions (RNA Protect Bacteria, Omnigene transport and 0.2% chlorhexidine) all yielded higher average Cq value than TE buffer control (p<0.05). This indicates that less total bacterial DNA was amplified under these three storage conditions compared to the control.

Figure 4C:
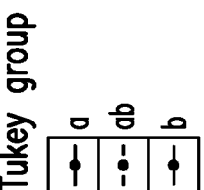
FIG. 4C is a graph depicting DNA concentration values measured by the Qubit marked by Tukey comparison group for samples stored using exemplary storage conditions A-F as described in Example 1.

For the qPCR assay, Peptostreptococcaceae sp. normalized to UniB relative to nothing, storage of the plaque impregnated sample collection device under all six conditions delivered measurable concentrations of Peptostreptococcaceae sp. DNA, as shown in FIG. 4B. Statistical comparisons indicated that all the storage conditions performed similarly with only a significant difference observed for the comparison between TE buffer and the Amies transport media (p<0.05) as shown in FIG. 4B. Similar results were obtained for total DNA yield, as measured using the Qubit, in that there was no significant difference between storage conditions with the exception of the Amies transport media which yielded less DNA than the Omnigene solution and 0.2% chlorohexidine (p<0.05) as shown in FIG. 4C. Based on DNA yield and the ability to detect Peptostreptococcaceae sp., the best performing storage condition under the exemplary test conditions was the dry sample collection device stored at room temperature for 5 days.

Discussion

The first of the two studies considered six different sample collection device options. The sample collection devices tested used heads with different material compositions, and as a result textures, and were identified as suitable candidates from the scientific literature. Plaque could be obtained from dogs' mouths using all of the sample collection devices tested. The highest quantity of DNA, total DNA measured using the Qubit and bacterial DNA measured using the UniB qPCR assay, was obtained using the Cytosoft cytology brush. However, the quantity of bacterial DNA obtained using the cytology brush was not significantly different to the foam, Dacron swabs or PurFlock® ultra swabs. With respect to total DNA yield, there was no significant difference between sample collection devices with the exception of the Rayon swab which had the lowest DNA concentration. The organism of interest, Peptostreptococcaceae sp., could be detected using all of the sample collection device types. The cytology brush also performed well on other parameters including the ease with which the technician could collect the sample and how straightforward it was for the laboratory to process the sample. The cytology brush was the only sample collection device tested with bristles. The bristles can enable the plaque to be captured between them, which is one explanation for the positive results.

The second study considered the effect of transit time and temperature on the bacterial composition of plaque. The bacterial population in a sample can continue to change after the sample is collected without stabilization in some instances, and transit time and temperature can be factors influencing change in bacterial population. The potential continued multiplication of the Peptostreptococcaceae sp. after sample collection can present challenges for a diagnostic based on quantifying the levels of this particular species. Comparison of the six conditions tested indicated that air-drying the plaque, and subsequent storage at room temperature, gave a high quantity of bacterial DNA, which was not significantly different to the TE buffer control that was stored at −80° C. for 5 days. In terms of total DNA as measured by Qubit, there was no significant difference between the sample collection devices tested, with the exception of the Amies transport medium which gave a lower yield of DNA under the exemplary test conditions. In terms of stability of the bacterium Peptostreptococcaceae sp., the relative abundance did not significantly differ between storage conditions with the exception of the Amies transport buffer where it was lower. Air-drying the sample collection device and transporting it for laboratory processing at ambient temperature provided positive results in the exemplary study, particularly given the overall safety and ease associated with a diagnostic kit lacking a liquid component.

Example 2

Bacterial Diversity Within the Canine Oral Microbiome

This example describes the bacterial diversity found within different oral niches in canines.

Methods

Samples of the oral microbiome were collected from the supragingival plaque, the buccal mucosa, the tongue dorsum mucosa and stimulated saliva from 14 Labrador retrievers at three timepoints within a one-month timeframe. The V3-V4 region of the 16S rRNA gene was sequenced using the MiSeq sequencing device (manufactured by Illumina). Right and left side buccal mucosa were sampled by gentle scraping of these areas with a CytoSoft™ cytology brush (manufactured by Medical Packaging Corporation). The posterior tongue dorsum mucosa was also sampled using a CytoSoft™ cytology brush.

Results and Conclusions

Figure 10:
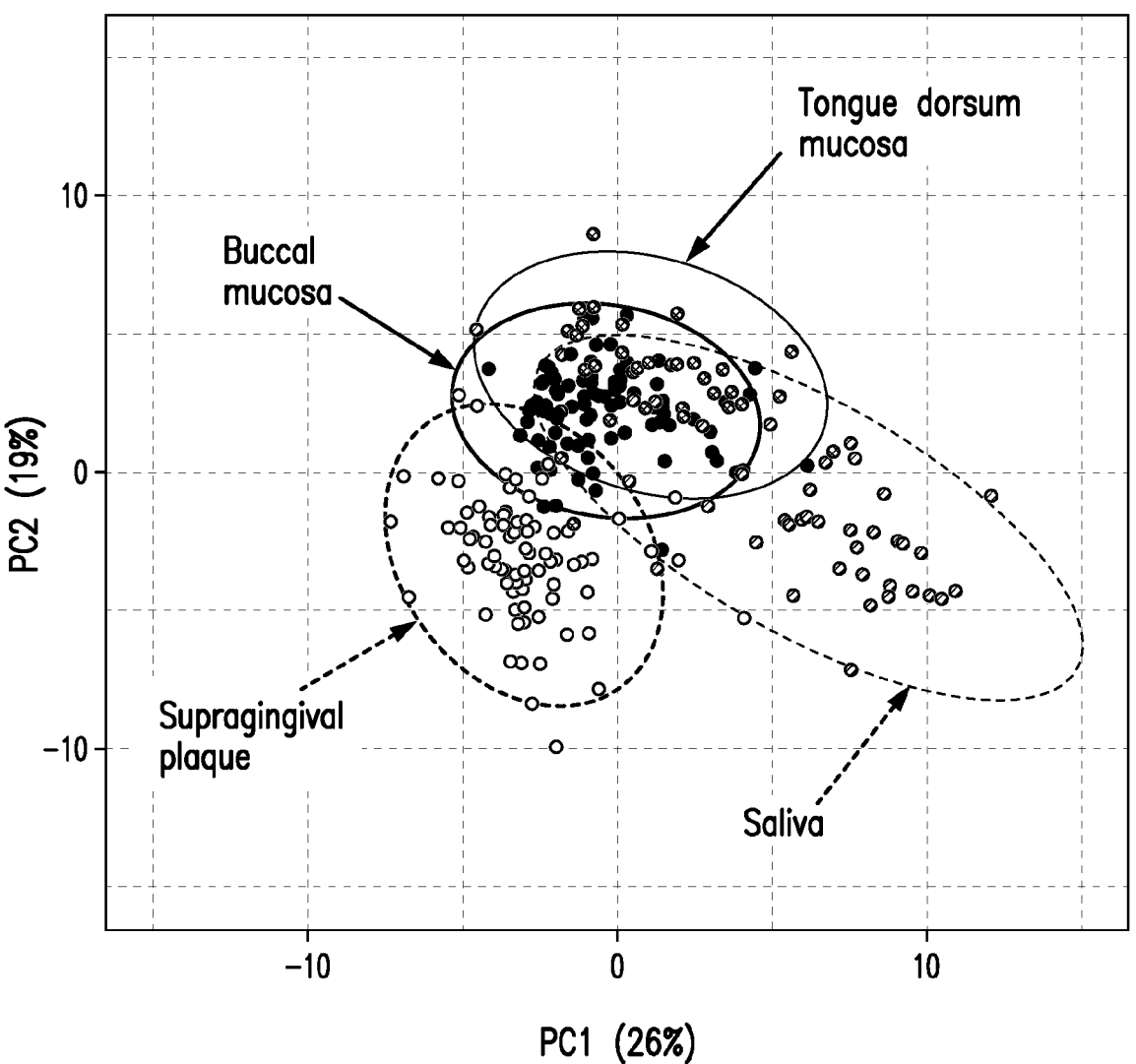
FIG. 10 is a graph showing principal component scores from analysis performed on the $\log_{10}$ proportions of operational taxonomic units identified in each of the oral niches: buccal mucosa, supragingival plaque, saliva and tongue dorsum mucosa.
Figure 11:
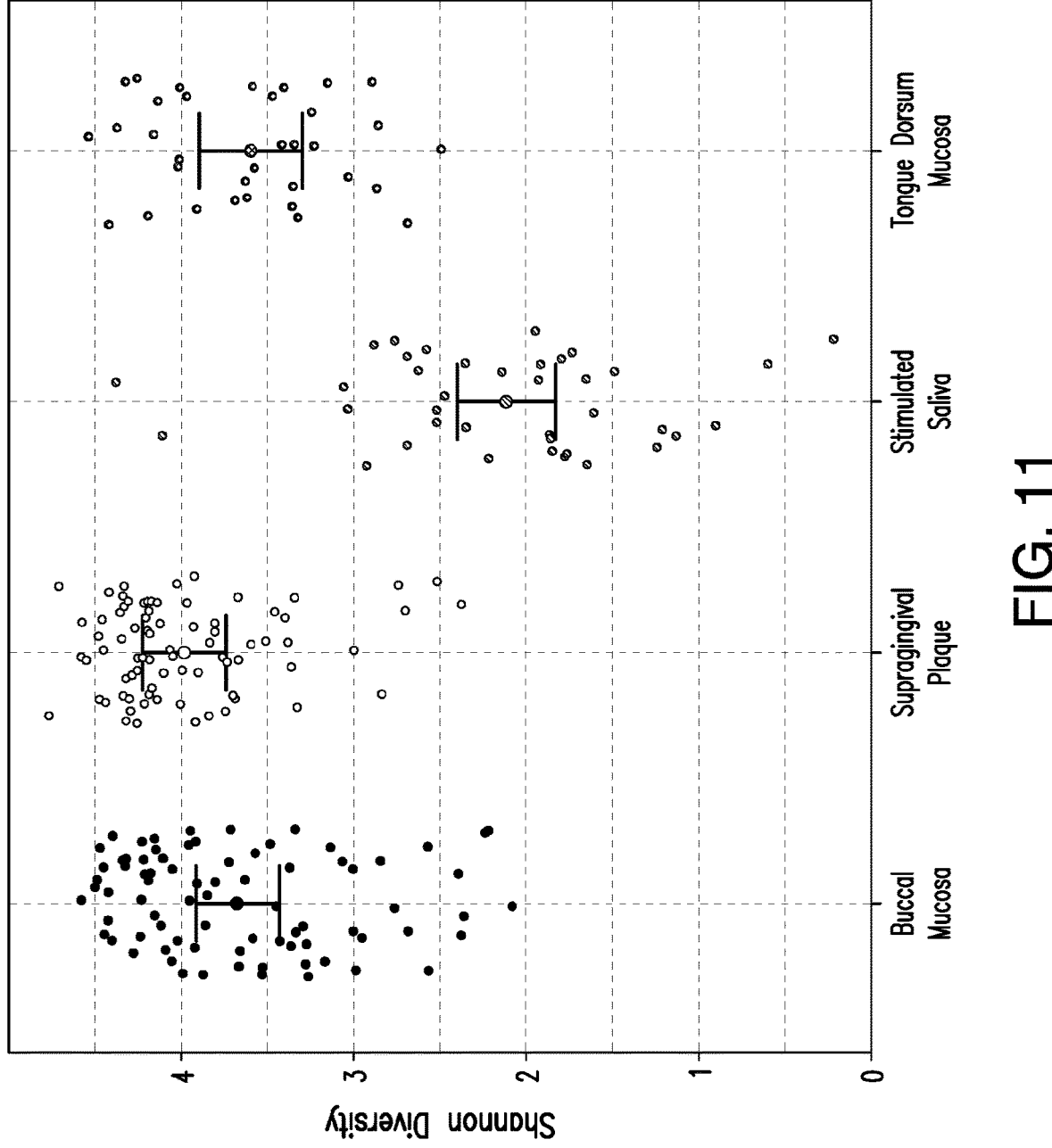
FIG. 11 is a graph showing the Shannon diversity index for samples from four niches within the dogs' mouth.

Supragingival plaque microbiota had the highest bacterial diversity and the largest number of significant differences in individual taxa when compared to the other oral niches (see, e.g., FIG. 11). Stimulated saliva exhibited the highest variability in microbial composition between dogs, yet the lowest bacterial diversity amongst all the niches. Overall, the bacteria of the buccal and tongue dorsum mucosa were most similar (see, e.g., FIG. 10).

The bacterial community profiles indicated three discrete oral niches: soft tissue surfaces (buccal and tongue dorsum mucosa), hard tissue surfaces (supragingival plaque) and saliva.

TABLE 7

Pairwise comparisons of canine oral niches showing the number of operational taxonomic units that significantly differed. Numbers indicated are out of 224 OTUs.

|  | p-values < 0.05 |
| --- | --- |
| Plaque/Buccal | 125 |
| Saliva/Buccal | 86 |
| Saliva/Plaque | 104 |
| Tongue/Buccal | 40 |
| Tongue/Plaque | 92 |
| Tongue/Saliva | 55 |

Example 3

Effects of Varying Storage Conditions on Bacterial Samples Collected from the Oral Microbiome of Canines This example further describes varying storage conditions relating to methods of collecting bacterial samples from the oral microbiome of canines.

Methods

Study Cohort

This study was conducted with plaque sampled weekly from a pool of 57 adult dogs, comprising Labrador retrievers, Beagles, Petite Basset Griffon Vendeens, and Norfolk terriers, aged between 1.2 and 8.3 years. Weekly, the study cohorts comprised 18-20 adult dogs. Dog size and age are putative risk factors for periodontitis and therefore sample associated metadata was also obtained (Table 8).

TABLE 8

Summary of metadata for the study cohort; numbers shown are mean ± s.d.

| | |
| --- | --- |
| Age | 4.9 ± 2.2 years |
| Gender | 35 female, 22 male |
| Neutered status | 51 yes, 6 no |
| Bodyweight | 27.3 ± 3.4 kg |
| Breed | Labrador Retriever, Beagle, Petit Basset Griffon Vendeen, Norfolk Terrier |

Sample Collection

Gingival margin plaque samples were collected by sweeping a swab just above the gum line on the outer buccal surface of teeth, from the canine to the fourth premolar (tooth numbers 04-09) on the upper and lower jaw of one half of the mouth. The nylon CytoSoft™ cytology brush (Medical Packaging Corporation) was used for all plaque collections throughout the study. Following sampling, plaque coated swabs were placed back in the original packaging for the collection swab. Individually packaged swabs were used for this study and samples from the left (LHS) and right (RHS) hand sides of the mouth per dog collected using two different swabs, processed separately downstream, as indicated in Table 9. Plaque collections from the LHS and RHS of the mouth were generally alternated between the test and control aspects of each week's objective or investigation. The swabs were subject to incubation at varying temperatures and for varying lengths of time to reflect potential real-life transit or postage conditions (Table 9). Following incubation, the swabs were placed into 1.5 mL microfuge tubes and claw clippers were used to cut the swab handle so that the plaque-coated swab would fit in the tubes with the lid closed. The samples were frozen at −80° C. and the DNA was extracted as described below.

TABLE 9

| Sample collection and processing summary. | | |
| --- | --- | --- |
| | Incubation: Test | Incubation: Control |
| A | RT, 14 days | RT, 5 days |
| B | 30° C., 5 days | RT, 5 days |
| C | 40° C., 5 days | RT, 5 days |
| D | 30° C., 14 days | RT, 5 days |
| E | 40° C., 14 days | RT, 5 days |

RT denotes sample incubations conducted at room temperature.

DNA Extraction

DNA was extracted from the plaque samples using a Masterpure™ Gram positive DNA purification kit according to the manufacturer's instructions with the addition of an overnight lysis (EpiCentre, catalogue #MGP04100). Plaque samples were centrifuged at 5000× g for 10 minutes and the bacterial pellet re-suspended in 150 μL TE buffer by vortexing. Ready-Lyse™ Lysozyme Solution (1 μL; Epicentre, catalogue #R1804M) was added to the bacterial suspension which was then incubated at 37° C. for 18 hours. Following DNA extraction the DNA pellet was re-suspended in TE buffer (10 mM Tris HCl and 0.5 mM pH 9.0 EDTA). The quantity of DNA was determined using a Qubit® dsDNA High Sensitivity Assay Kit (Thermo Fisher Scientific, Inc.).

Quantitative PCR (qPCR) Analyses

An assay was developed against the 16S rRNA gene of Peptostreptococcaceae sp. and a universal qPCR assay (UniB).

Each individual 10 μL quantitative PCR (qPCR) reaction contained: 5 μL Applied Biosytems Gene Expression Taqman MasterMix (Applied Biosystems, USA), 0.5 μL 20× concentrated assay, 1 μL 1:10 dilution of DNA and 3.5 μL nuclease-free water. Each assay contained a final concentration of 900 nM of each primer and 250 nM of each qPCR probe per reaction. Experiments were performed in triplicate. Positive and negative controls, also included in triplicate, were the M13 purified amplicon of Peptostreptococcaceae sp. clone DNA at 0.001 ng/μL and nuclease-free water, respectively. Data were collected on an AB7900 HT machine (Applied Biosystems, USA) and analyzed using GenEx software (MultiD, Sweden).

Peptostreptococcaceae sp. assay normalized to UniB relative to nothing was calculated by performing the following equation on the mean, efficiency corrected Cq value for each sample: $2^{-(mean\ Peptostreptococcaceae\ spCq\ value-mean\ UniB\ Cq\ value)}$.

Statistical Analysis

Each week tested either a different swab condition or a different time for the sample to be taken and the data was split by the different weeks. A linear mixed effects model with the relative Peptostreptococcaceae sp. assay linearized to nothing on the log10 scale, a random effect of individual dog and a fixed effect of the condition variable was fitted.

The coefficients were back transformed (10^) to obtain the mean estimates. Since the contrasts were compared to a control, a Dunnett's test was used for the contrasts. The estimates were back transformed to obtain the fold change between the test condition and the control.

All analyses were performed using R version 3.6.1. libraries used were ggplot2, lmec, DT, multcomp and lme4.

Results

Effect of Storage Timeframes

Figure 5:
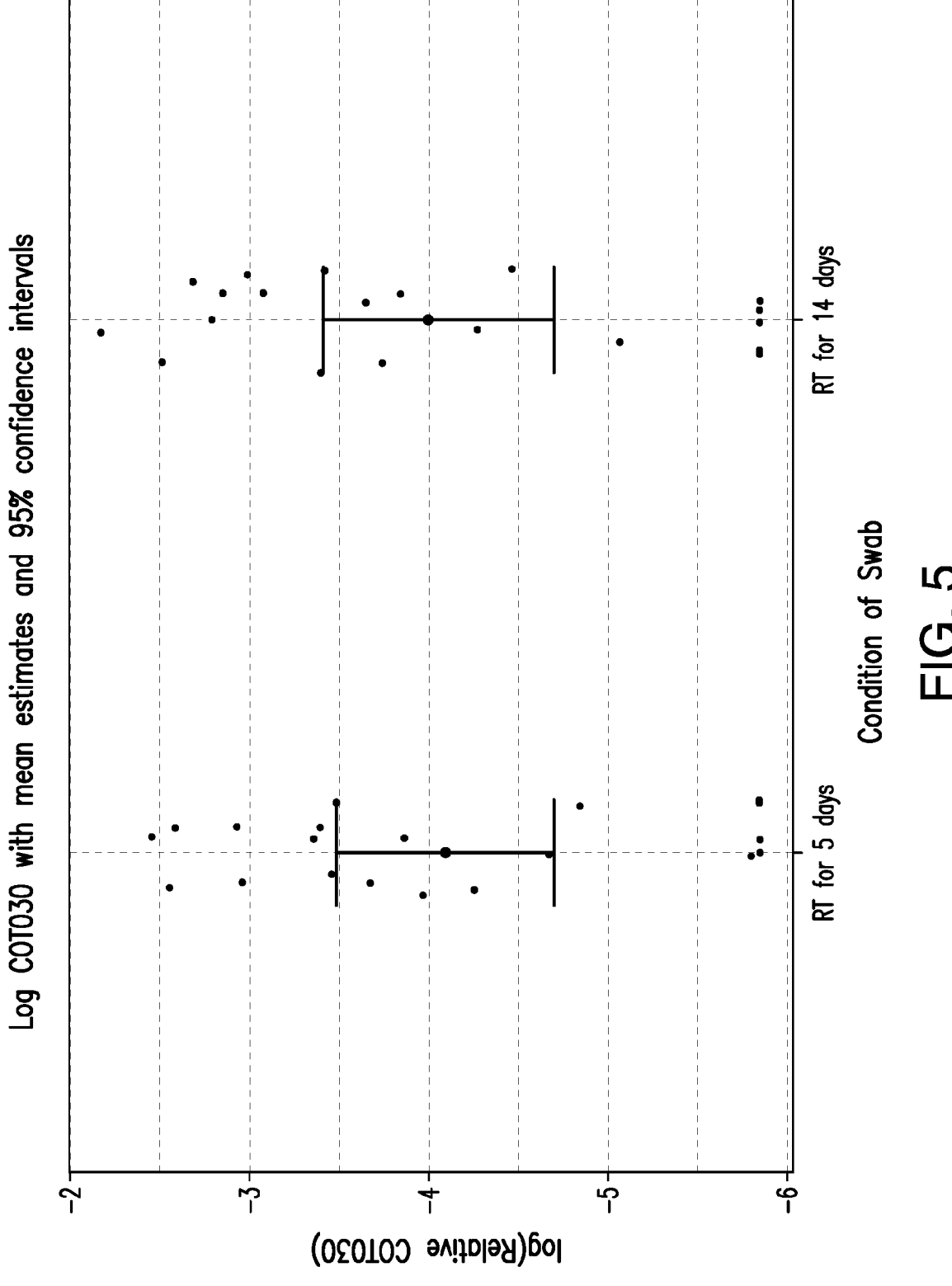
FIG. 5 is a graph showing the means and 95% confidence intervals for Peptostreptococcaceae sp. Cq normalized to UniB Cq relative to nothing when comparing storing the sample for 14 days versus 5 days at room temperature.

Previous studies analyzed the effect of storage conditions on the plaque samples and corresponding qPCR analyses with samples being kept at room temperature (RT) for approximately 5 days. Here, timeframes of 14 days were studied and were compared to a control scenario of 5 days, both at RT. The results expressed as Peptostreptococcaceae sp. normalized to UniB relative to nothing are shown in FIG. 5. The difference between the timeframes, in each instance, were not found to be significant different (p>0.6) between 14 and 5 days.

Effect of Storage Temperatures

Figure 6:
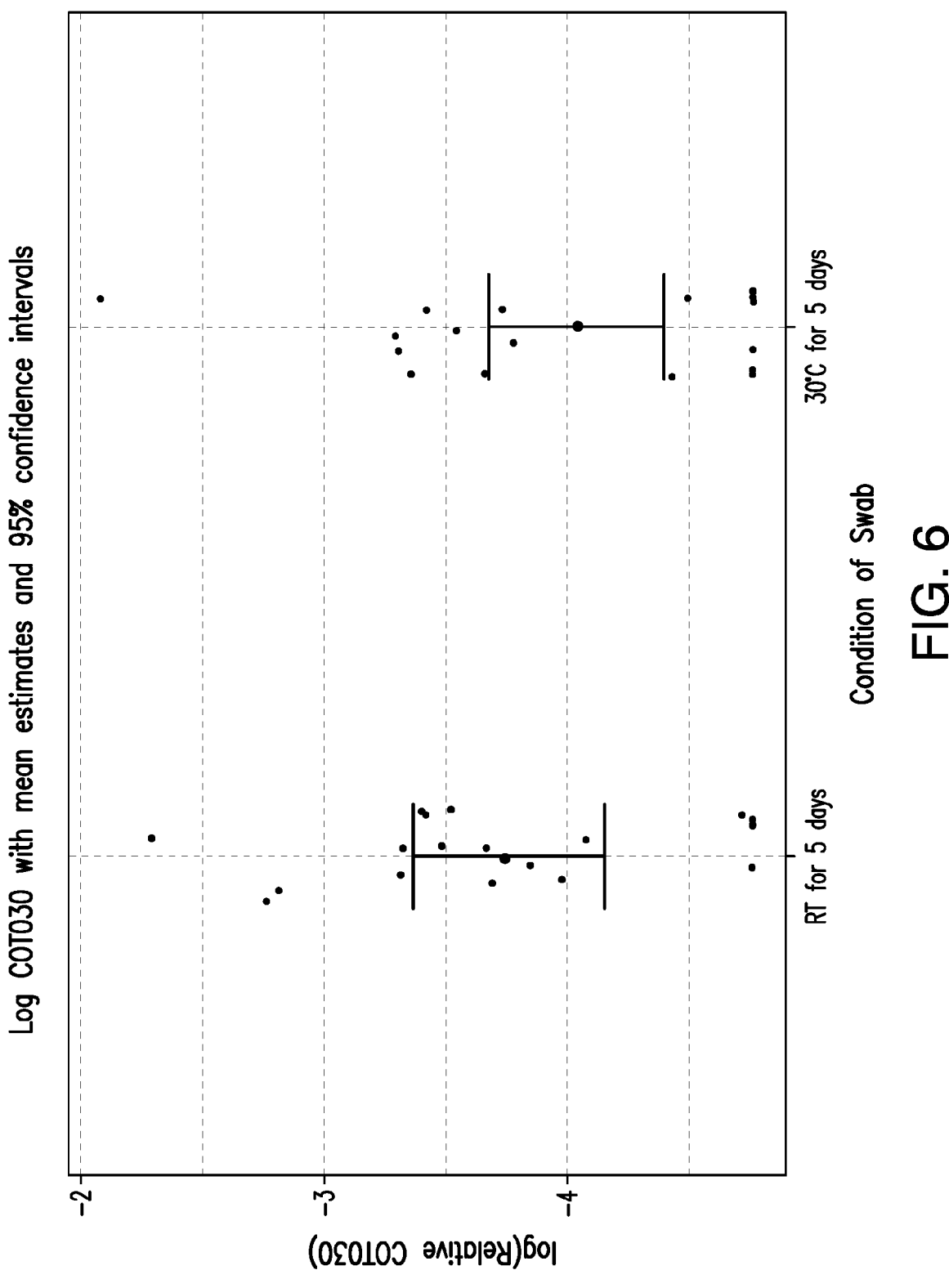
FIG. 6 is a graph showing the means and 95% confidence intervals for Peptostreptococcaceae sp. Cq normalized to UniB Cq relative to nothing when comparing storing the sample at 30° C. versus room temperature for 5 days.
Figure 7:
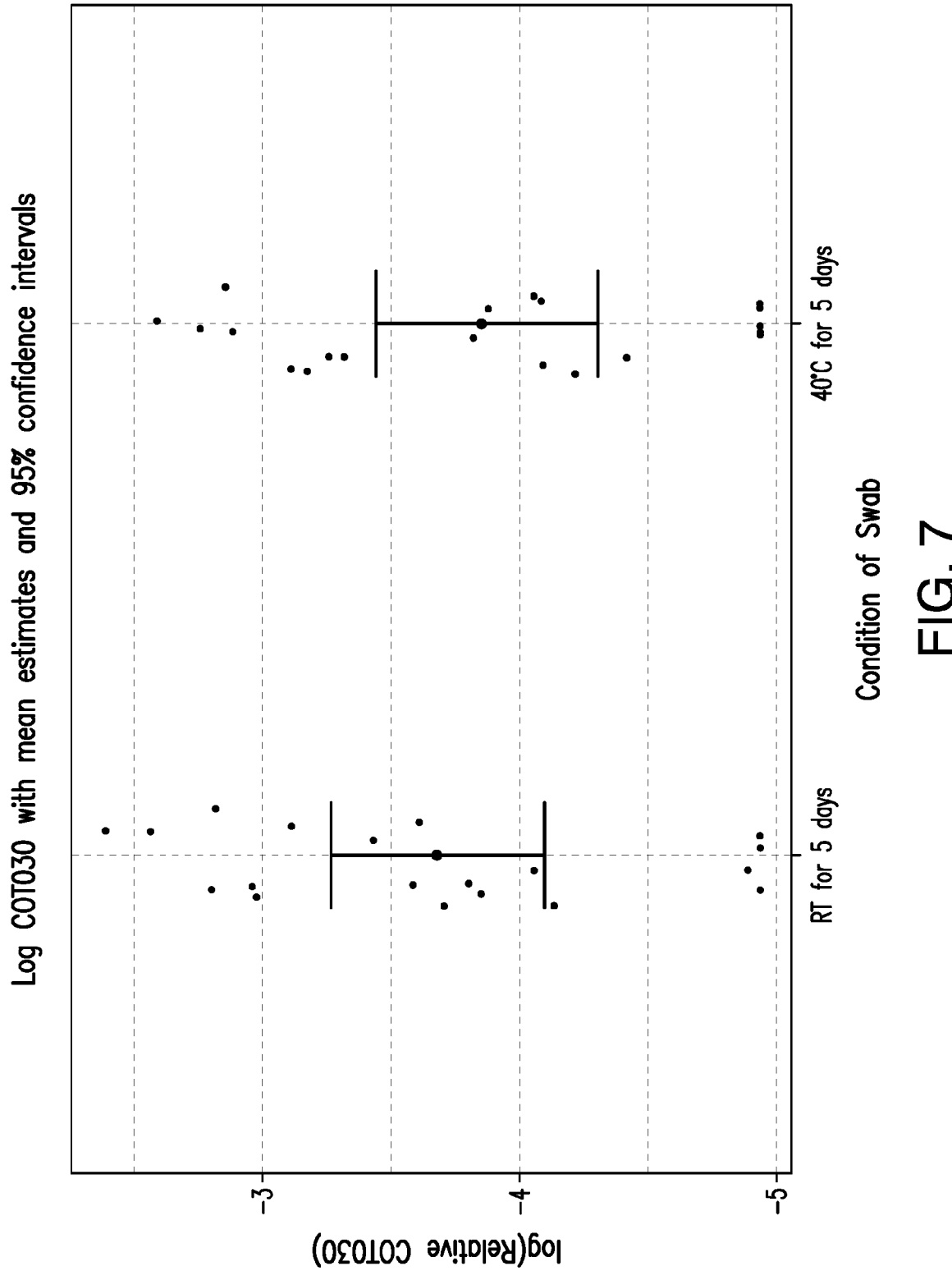
FIG. 7 is a graph showing the means and 95% confidence intervals for Peptostreptococcaceae sp. Cq normalized to UniB Cq relative to nothing when comparing storing the sample at 40° C. versus room temperature for 5 days.

The effect of differing temperature conditions were also explored in the following study. Higher temperatures were investigated by incubating the plaque samples at 30° C. and 40° C., whilst maintaining the incubation timeframe at 5 days. In each instance, the control plaque samples were retained at RT for 5 days, prior to freezing and subsequent laboratory processing. The resulting comparison of the qPCR outputs for these investigations is shown in FIGS. 6 and 7. The temperatures tested were found to have no impact, with the differences observed in contrast to the relative 5 day incubations at RT, in each instance, not significant (p>0.2).

Combined Effect of Storage Temperatures and Timeframes

Figure 8:
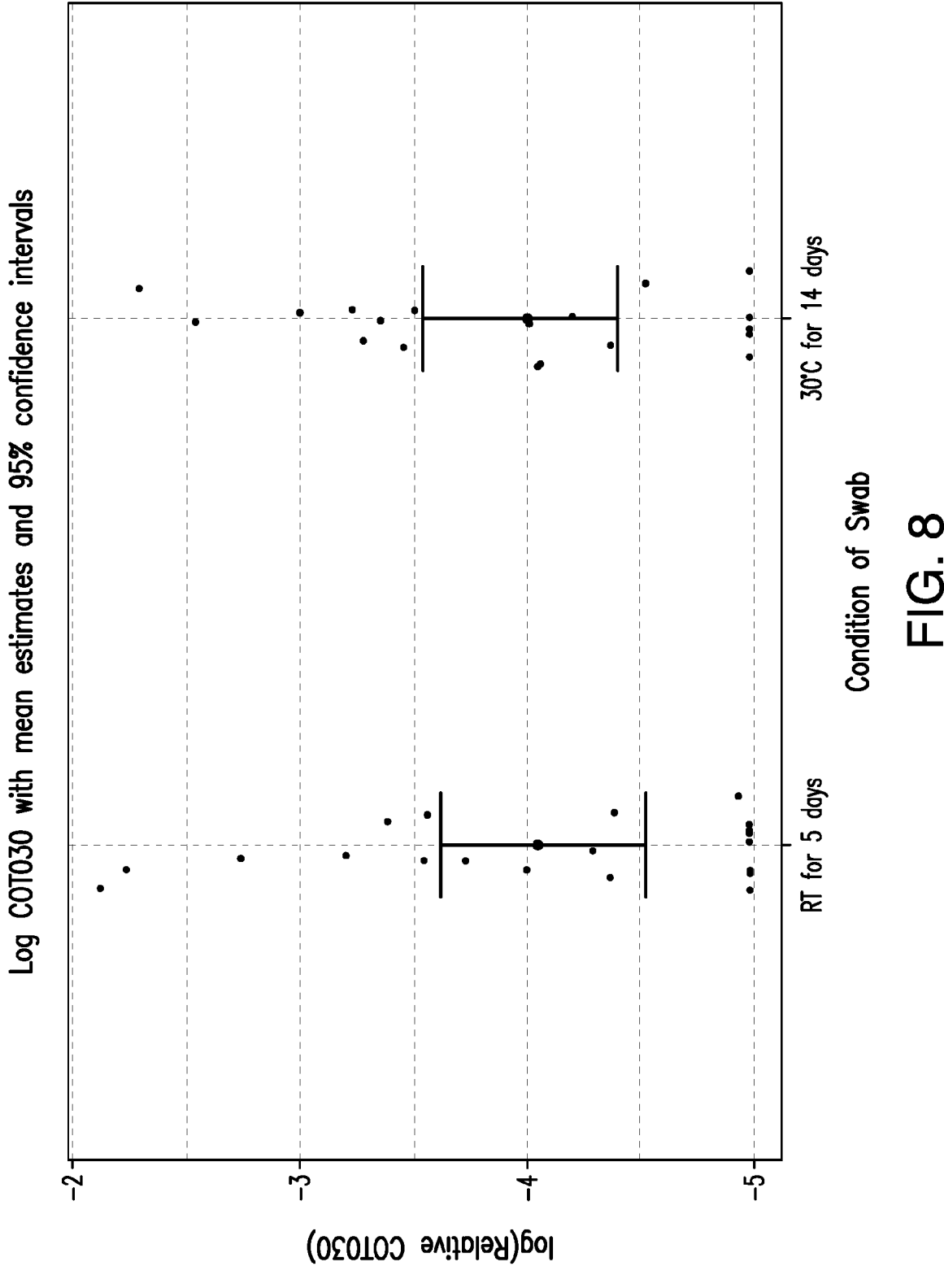
FIG. 8 is a graph showing the means and 95% confidence intervals for Peptostreptococcaceae sp. Cq normalized to UniB Cq relative to nothing when comparing storing the sample at 30° C. for 14 days versus room temperature for 5 days.
Figure 9:
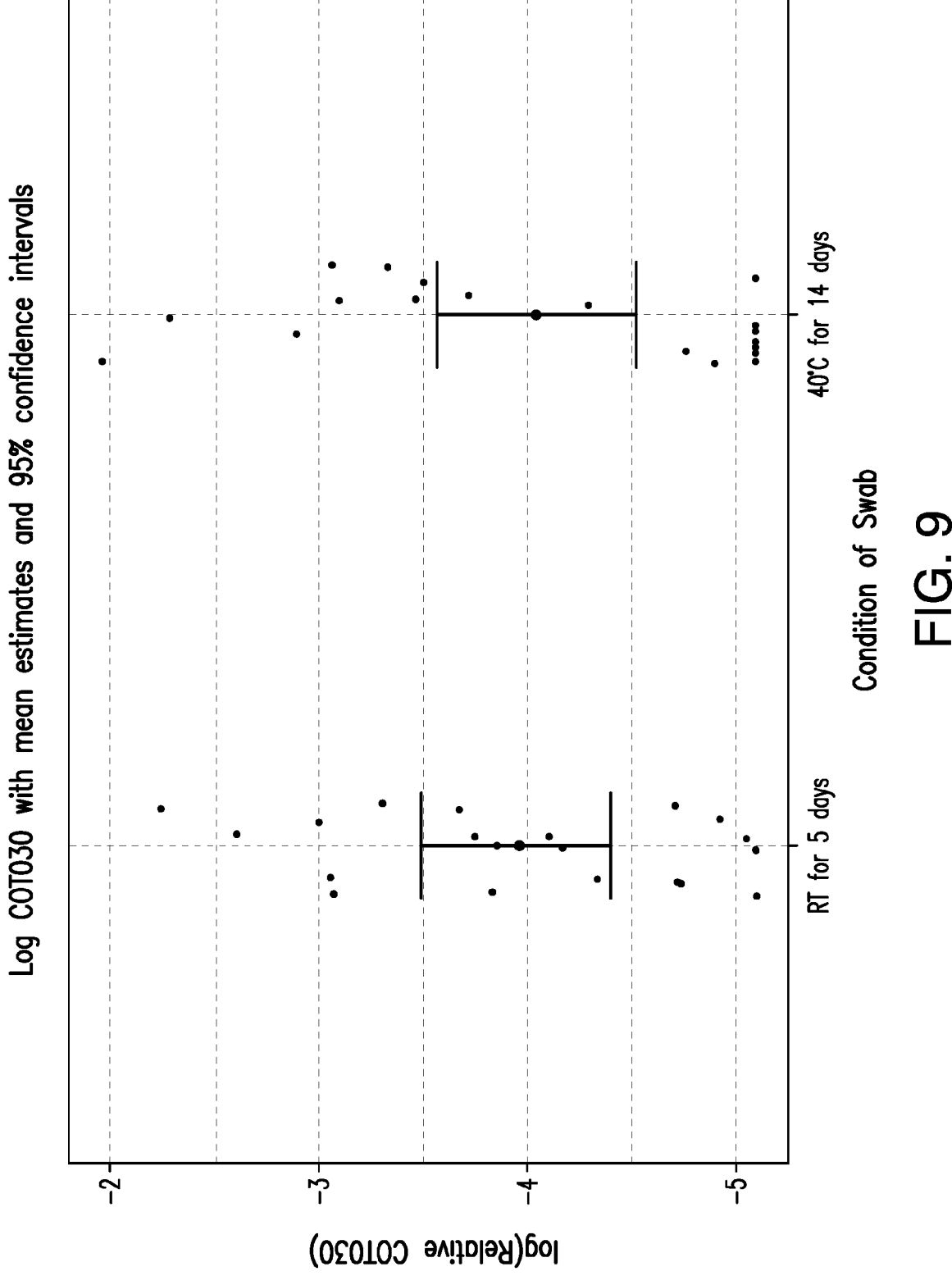
FIG. 9 is a graph showing the means and 95% confidence intervals for Peptostreptococcaceae sp. Cq normalized to UniB Cq relative to nothing when comparing storing the sample at 40° C. for 14 days versus room temperature for 5 days.

The plaque sample timeframe and temperature storage conditions tested above, as single conditions changes, were integrated to allow the potential impact of combined changed to be assessed together. The higher 30° C. and 40° C. temperatures were combined with the extended timeframe of 14 days, and the comparable test control of RT for 5 days used in both instances. The qPCR outputs of these comparisons are shown in FIGS. 8 and 9. As observed in the independent single change investigations reported above, the findings indicated the comparisons of the combined sample investigation were additionally not significantly different from samples subject to 5 days at RT (p>0.2). This means there was no impact of incubating the samples at 30° C. or 40° C. for 14 days.

Discussion

The outputs from the Peptostreptococcaceae sp. qPCR assay(s) indicated that the timeframe or temperature storage conditions tested did not differ significantly from the conditions previously tested (RT for 5 days). The results demonstrate that the plaque sample collected for the purpose of testing with the oral care diagnostic is stable under conditions up to 40° C. and 14 days, without negative consequences on the test outputs. The results of the combined temperature and time test were very surprising, as it was not expected that incubation in the relatively extreme environment of 40° C. for 14 days would not be significantly different from incubation at much lower temperatures and much shorter times, i.e., RT for 5 days. For instance, it was speculated that the outputs of the qPCR assay could have been altered by the continued proliferation of Peptostreptococcaceae sp. or population of the sample by other bacteria, yet this was not observed in this study. Furthermore, it is noted that the environment on the swab in the dry container is very different from the environment within a dog's mouth, especially given that there are no micronutrients present on the swab. There was no expectation that the conditions within a dog's mouth could correlate to the conditions in which a swab was stored. These are important findings given the conditions for investigation were roughly doubled from a temperature perspective and almost tripled from a timeframe perspective. The results place confidence in the ability to accurately assess the plaque sample obtained for periodontal disease risk across world geographies.

Dogs used herein included Labrador Retriever, Beagle, Petite Basset Griffon Vendeen, Norfolk Terrier, spanning large, medium and small breed categories to demonstrate that this test is effective for analysis from a range of different breed sizes.

REFERENCES

1. Lund, E. M., et al., Health status and population characteristics of dogs and cats examined at private veterinary practices in the United States. J Am Vet Med Assoc, 1999. 214(9): p. 1336-1341.
2. O'Neill, D. G., et al., Prevalence of disorders recorded in dogs attending primary-care veterinary practices in England. PLoS One, 2014. 9(3): p. e90501.
3. Hamp, S. E., et al., A macroscopic and radiological investigation of dental diseases of the dog. Veterinary Radiology, 1984. 25(2): p. 86-92.
4. Butković, V., et al., *Dental diseases of dogs: a retrospective study of radiological data*. Acta Veterinaria Brno, 2001. 70(2): p. 203-208.
5. Kortegaard, H. E., T. Eriksen, and V. Baelum, *Periodontal disease in research beagle dogs—an epidemiological study*. J Small Anim Pract, 2008. 49(12): p. 610-616.
6. Hoffman, T. and P. Gaengler, *Epidemiology of periodontal disease in poodles*. Journal of Small Animal Practice, 1996. 37: p. 309-316.
7. Dewhirst, F. E., et al., The canine oral microbiome. PLoS One, 2012. 7(4): p. e36067.
8. Dewhirst, F. E., et al., The feline oral microbiome: a provisional 16S rRNA gene based taxonomy with full-length reference sequences. Vet Microbiol, 2015. 175 (2-4): p. 294-303.
9. Riggio, M. P., et al., Molecular identification of bacteria associated with canine periodontal disease. Vet Microbiol, 2011. 150(3-4): p. 394-400.
10. Davis, I. J., et al., A cross-sectional survey of bacterial species in plaque from client owned dogs with healthy gingiva, gingivitis or mild periodontitis. PLoS One, 2013. 8(12): p. e83158.
11. Wallis, C., et al., A longitudinal assessment of changes in bacterial community composition associated with the development of periodontal disease in dogs. Vet Microbiol, 2015. 181(3-4): p. 271-82.
12. Harris, S., et al., A Pyrosequencing Investigation of Differences in the Feline Subgingival Microbiota in Health, Gingivitis and Mild Periodontitis. PLoS One, 2015. 10(11): p. e0136986.

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

The invention claimed is:

1. A system comprising:
a kit to test an oral microbiome of an animal, the kit comprising:
a sample collection device having a handle and a head opposite the handle, the head comprising a plurality of bristles extending over an outer surface of the head, the handle including a first end and a second end proximate the head with a longitudinal axis defined therebetween, and wherein the sample collection device is configured to swab a part of an oral cavity of an animal and to collect a sample therefrom, wherein the plurality of bristles are configured to capture sample between respective bristles, wherein the sample collection device includes a cytology brush, and
a dry container without a buffer therein for storing the sample collection device therein, the dry container including a bottom segment couplable with a top segment to wholly house the sample collection device therein, the dry container having an open position for receiving at least the head in the top segment, and a closed position for receiving the head and the handle therein, wherein the dry container defines an aperture disposed at the top segment adjacent to the head to permit communication between an inside of the dry container with an external environment, wherein at least a portion of the handle is disposed within the bottom segment, wherein the sample collection device having a sample captured thereon and disposed in the dry container with the aperture protects stability of the sample for up to 14 days and up to 40 degrees Celsius, wherein, in the closed position, the top segment is configured to house the second end of the handle and an entirety of the head and the bottom segment is configured to house the first end of the handle; and
reagents for performing a qPCR assay against a 16S rRNA gene of at least one of Peptostreptococcaceae XIII [G-1] sp., Peptostreptococcaceae COT-030, Peptostreptococcaceae COT-005/004, Peptostreptococcaceae COT-047, and/or Peptostreptococcaceae COT-019, the qPCR assay configured to determine a relative abundance of Peptostreptococcaceae sp. in the oral microbiome of the animal based on the sample.

2. The system of claim 1, wherein a longitudinal axis of the head is disposed at an angle with respect to the longitudinal axis of the handle between approximately 90 degrees and 170 degrees thereto.

3. The system of claim 1, wherein the head has a cylindrical shape.

4. The system of claim 1, wherein the head has a length dimension measured along a longitudinal axis, wherein the length dimension is between approximately 1.5 cm and 2.5 cm.

5. The system of claim 1, wherein the head comprises at least one of a nylon, polyester, rayon, and combinations thereof.

6. The system of claim 1, wherein the plurality of bristles extend over 360 degrees of the outer surface of the head.

7. The system of claim 1, wherein a length dimension of the plurality of bristles is between approximately 1.5 mm and 5 mm.

8. The system of claim 7, wherein the length dimension of the plurality of bristles tapers from the first end of the head to the second end of the head, the plurality of bristles defining a conical shape.

9. The system of claim 1, wherein the plurality of bristles extending around a circumference of the head and the bristles define a conical shape proximate to the first end of the handle, the bristles tapering in length from a first end of the head proximate to the first end of the handle to a second end of the head, and wherein the handle includes a cylindrical shape adjacent to the conical shape.

10. A method of collecting a sample from an oral cavity of an animal, the method comprising:
    (i) providing a kit including:
        (a) a sample collection device having a handle and a head opposite the handle, the head comprising a plurality of bristles extending over an outer surface of the head, the handle including a first end and a second end with a longitudinal axis defined therebetween, and wherein the sample collection device is configured to brush a part of the oral cavity of the animal and to collect the sample therefrom, wherein the plurality of bristles are configured to capture the sample between respective bristles, and
        (b) a dry container without a buffer therein for storing the sample collection device therein, the dry container including a bottom segment couplable with a top segment to wholly house the sample collection device therein, the dry container having an open position for receiving at least the head in the top segment, and a closed position for receiving the head and the handle therein, wherein the dry container defines an aperture disposed at the top segment adjacent to the head to permit communication between an inside of the dry container with an external environment, wherein at least a portion of the handle is disposed within the bottom segment, wherein the sample collection device having a sample captured thereon and disposed in the dry container with the aperture protects stability of the sample for up to 14 days and up to 40 degrees Celsius;
    (ii) brushing at least one of gums, a gum-line, teeth, a tongue, a roof of a mouth, and/or another part of the oral cavity of the animal with the sample collection device to collect the sample thereon and between respective bristles; and
    (iii) drying the head and storing the sample collection device in the dry container for a duration of 5 days up to 14 days and up to 40 degrees Celsius.

11. The method of claim 10, wherein the method further comprises (iv) performing an assay on the sample to measure an amount of a microbial nucleic acid to detect one or more bacteria in the sample and/or to measure an amount of one or more bacteria in the sample, wherein the sample collection device includes a cytology brush, and wherein in the closed position, the top segment is configured to house the second end of the handle and an entirety of the head and the bottom segment is configured to house the first end of the handle.

12. A method of detecting one or more bacteria in an oral microbiome of a canine, the method comprising:
    (i) providing a first kit including:
        (a) a first sample collection device of a first type having a handle and a head opposite the handle, the first sample collection device configured to brush at least one of gums, a gum-line, teeth, a tongue, a roof of a mouth, and/or another part of an oral cavity of a canine to collect a first sample, and
        (b) a first dry container for storing the first sample collection device therein while drying the head of the first sample collection device, the first dry container having an open position for receiving at least the head and a closed position, wherein the first dry container defines an aperture to permit communication between an inside of the first dry container with an external environment, wherein the first sample collection device having a sample captured thereon and disposed in the first dry container with the aperture protects stability of the sample for up to 14 days and up to 40 degrees Celsius;
    (ii) providing a second kit including:
        (a) a second sample collection device of a second type having a handle and a head opposite the handle, the second sample collection device configured to brush at least one of gums, a gum-line, teeth, a tongue, a roof of a mouth, and/or another part of the oral cavity of the canine to collect a second sample, and
        (b) a second dry container for storing the second sample collection device therein while drying the head of the second sample collection device, the second dry container having an open position for receiving at least the head and a closed position, wherein the second dry container defines an aperture to permit communication between an inside of the second dry container with the external environment, wherein the second sample collection device having a sample captured thereon and disposed in the second dry container with the aperture protects stability of the sample for up to 14 days and up to 40 degrees Celsius;
    (iii) collecting the first sample using the first sample collection device by brushing at least one of gums, a gum-line, teeth, a tongue, a roof of a mouth, and/or another part of the oral cavity of the canine,
        (a) storing the first sample collection device within the first dry container for 5 days up to 14 days;
    (iv) collecting the second sample using the second sample collection device by brushing at least one of gums, a gum-line, teeth, a tongue, a roof of a mouth, and/or another part of the oral cavity of the canine,
        (a) storing the second sample collection device within the second dry container for 5 days up to 14 days;
    (v) performing a first assay on the first sample to measure a first value, the first value being an amount of a microbial nucleic acid to detect the one or more bacteria and/or to measure an amount of the one or more bacteria in the first sample;
    (vi) performing a second assay on the second sample to measure a second value, the second value being an amount of a microbial nucleic acid to detect the one or more bacteria and/or to measure an amount of the one or more bacteria in the second sample;

wherein the first assay and the second assay are a qPCR assay against a 16S rRNA gene of the one or more bacteria selected from a group consisting of *Peptostreptococcus* sp., *Synergistes* sp., Clostridiales sp., *Eubacterium nodatum, Selenomonas* sp., Bacteroidetes sp., *Odoribacter denticanis, Desulfomicrobium ovale, Moraxella* sp., *Bacteroides* denticanoris, Fillifactor *villosus, Porphyromonas canoris, Porphyromonas gulae, Treponema denticola*, and *Porphyromonas salivosa;*

(vii) comparing the first value and the second value to determine a relative abundance of Peptostreptococcaceae sp. in canine oral microbiome for each of the first sample and second sample; and (viii) diagnosing a likelihood of the canine having an oral disease or disorder based on the abundance of the Peptostreptococcaceae sp. in the oral microbiome of the canine;

wherein the bacteria of the Peptostreptococcaceae sp. are selected from the group consisting of Peptostreptococcaceae XIII [G-1] sp., Peptostreptococcaceae COT-030, Peptostreptococcaceae COT-005/004, Peptostreptococcaceae COT-047, and/or Peptostreptococcaceae COT-019.

13. The method of claim 12, wherein the first sample is collected at a first time and the second sample is collected at a second time, wherein the first sample collection device includes a cytology brush, wherein the second sample device includes a cytology brush, and wherein the method further comprises recommending a change in oral hygiene or an intervention if a difference between the first value and the second value is indicative of worsening oral health.

14. The method of claim 13, wherein the intervention comprises cleaning a mouth of the canine, removing plaque from the mouth of the canine, polishing teeth of the canine, scaling the teeth to remove tartar or calculus, performing a gingivectomy, removing one or more diseased teeth from the mouth of the canine, administering an antibiotic, an anti-inflammatory drug, and/or an analgesic to treat an oral infection, providing dental chews to the canine or increasing a frequency of dental chews, introducing or increasing a frequency of non-edible chewing toys and dispensers, introducing or increasing a frequency of tooth brushing, increasing use of dental diets, providing a dental treatment solution in water, or any combination thereof.

15. The method of claim 12, wherein:

collecting the first sample comprises collecting supragingival plaque samples by sweeping the first sample collection device above a gumline on an outer buccal surface of teeth; and collecting the second sample comprises collecting buccal mucosa samples by scraping an inner lining of a cheek using the second sample collection device.

16. The method of claim 12, wherein:

collecting the first sample comprises collecting supragingival plaque samples by sweeping the first sample collection device above a gumline on an outer buccal surface of teeth; and collecting the second sample comprises collecting tongue dorsum mucosa samples by scraping an upper surface of the tongue using the second sample collection device.

17. The method of claim 12, further comprising:

(ix) determining bacterial variability across the collected first and second samples by comparing first and second values of several types of bacteria in the collected first and second samples; and (x) applying a principal component analysis (PCA) for the first and second values resulting in a first principal component and a second principal component for each sample from the first and second samples.

18. The method of claim 17, further comprising:

(xi) determining a PCA scatter plot; and (xii) based on the PCA scatter plot determining regions representing clustering of the collected first and second samples.

19. The method of claim 12, wherein the head of the first sample collection device comprises a plurality of bristles extending over an outer surface of the head and the plurality of bristles are configured to capture the first sample between respective bristles, wherein the first dry container includes a bottom segment couplable with a top segment to wholly house the first sample collection device therein, wherein at least a portion of the handle of the first sample collection device is disposed within the bottom segment of the first dry container and the first dry container does not have a buffer therein, wherein in the closed position, the top segment is configured to house a second end of the handle and an entirety of the head and the bottom segment is configured to house a first end of the handle.

* * * * *